US012721555B2

(12) United States Patent
Ohara

(10) Patent No.: US 12,721,555 B2

(45) Date of Patent: Sep. 1, 2026

(54) DETECTION DEVICE AND METHOD FOR MANUFACTURING SAME

(71) Applicant: Japan Display Inc., Tokyo (JP)

(72) Inventor: Ken Ohara, Tokyo (JP)

(73) Assignee: Japan Display Inc., Tokyo (JP)

(*) Notice: Subject to any disclaimer, the term of this patent is extended or adjusted under 35 U.S.C. 154(b) by 653 days.

(21) Appl. No.: 18/105,425

(22) Filed: Feb. 3, 2023

(65) Prior Publication Data

US 2023/0255524 A1 Aug. 17, 2023

(30) Foreign Application Priority Data

Feb. 15, 2022 (JP) ................................ 2022-021386

(51) Int. Cl.
*A61B 5/1455* (2006.01)

(52) U.S. Cl.
CPC ................................ *A61B 5/14552* (2013.01)

(58) Field of Classification Search
CPC ........ A61B 5/14552; A61B 2562/0233; A61B 5/1171; A61B 5/6824; A61B 5/489; A61B 5/6826
See application file for complete search history.

(56) References Cited

U.S. PATENT DOCUMENTS

| | | | | |
|---|---|---|---|---|
| 2015/0201875 A1* | 7/2015 | Tateda | A61B 5/6826 600/324 |
| 2022/0096007 A1* | 3/2022 | Robinson | A61B 5/02438 |
| 2023/0081794 A1* | 3/2023 | Mäkinen | A61B 5/681 356/614 |

FOREIGN PATENT DOCUMENTS

| | | | |
|---|---|---|---|
| JP | 2011-092452 A | 5/2011 | |

* cited by examiner

*Primary Examiner* — Abid A Mustansir

(74) *Attorney, Agent, or Firm* — K&L Gates LLP

(57) ABSTRACT

A detection device includes a housing, a light source provided in the housing, an optical sensor provided in the housing, a plurality of line-shaped first light guides provided in the housing and capable of guiding light emitted by the light source, and a plurality of line-shaped second light guides provided in the housing and capable of receiving the light guided by the first light guides and guiding the received light to the optical sensor.

7 Claims, 16 Drawing Sheets

DETECTION DEVICE AND METHOD FOR MANUFACTURING SAME

CROSS-REFERENCE TO RELATED APPLICATION

This application claims the benefit of priority from Japanese Patent Application No. 2022-021386 filed on Feb. 15, 2022, the entire contents of which are incorporated herein by reference.

BACKGROUND

1. Technical Field

The present disclosure relates to a detection device and a method for manufacturing the same.

2. Description of the Related Art

Devices are known that detect information on a living body from a human body. Japanese Patent Application Laid-open Publication No. 2011-092452 discloses that a state of the living body is measured while reducing the restraint of a user during measurement by widening the detection area for biometric information using two fibers, that is, a light-receiving fiber and a light-receiving fiber.

Conventional detectors enable the measurement by widening the detection area, but require a fingertip as a biological part to be simultaneously in contact with both the optical fibers, which may reduce measurement accuracy depending on the position touched by the fingertip, the state of the contact, and so forth. Therefore, in conventional measurement of the biometric information, there is a need for improvement in the measurement accuracy of the biometric information when the detectors are each worn on the living body that is a measurement target.

It is an object of the present disclosure to provide a detection device capable of improving the measurement accuracy of the biometric information when the device is worn on the measurement target, and provide a method for manufacturing the same.

SUMMARY

A detection device according to an embodiment of the present disclosure includes a housing, a light source provided in the housing, an optical sensor provided in the housing, a plurality of line-shaped first light guides provided in the housing and capable of guiding light emitted by the light source, and a plurality of line-shaped second light guides provided in the housing and capable of receiving the light guided by the first light guides and guiding the received light to the optical sensor. A light-receiving portion at one end of each of the first light guides faces the light source so as to be capable of receiving the light emitted by the light source, and a light-emitting portion at another end of each of the first light guides projects from inside the housing, and a light-receiving portion at one end of each of the second light guides projects from inside the housing, and a light-emitting portion at another end of each of the second light guides faces the optical sensor.

A method for manufacturing a detection device according to an embodiment is disclosed. The detection device includes a housing, a light source provided in the housing, an optical sensor provided in the housing, a plurality of line-shaped first light guides provided in the housing and capable of guiding light emitted by the light source, and a plurality of line-shaped second light guides provided in the housing and capable of receiving the light guided by the first light guides and guiding the received light to the optical sensor, and the method includes forming an arrangement member on which the first light guides and the second light guides configured to guide the light from the light source to the optical sensor are arranged, and forming the housing by filling a periphery of the arrangement member with a filling member.

DETAILED DESCRIPTION

Figure 1:
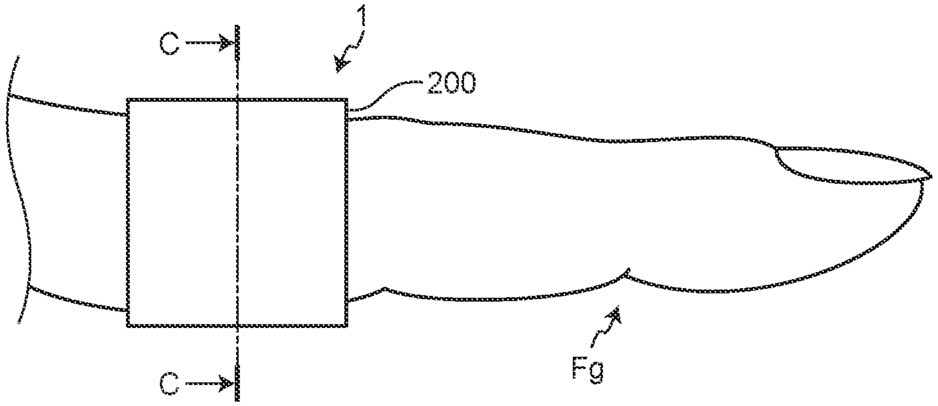
FIG. 1 is a schematic view illustrating an example of an external view of a state where a finger is accommodated in a detection device according to a first embodiment, as viewed from a lateral side of a housing.

The following describes modes (embodiments) for carrying out the present disclosure in detail with reference to the drawings. The present disclosure is not limited to the description of the embodiments to be given below. Components to be described below include those easily conceivable by those skilled in the art or those substantially identical thereto. In addition, the components to be described below can be combined as appropriate. What is disclosed herein is merely an example, and the present disclosure naturally encompasses appropriate modifications easily conceivable by those skilled in the art while maintaining the gist of the disclosure. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the description and the drawings, and detailed description thereof may not be repeated where appropriate.

In the present specification and claims, in expressing an aspect of disposing another structure above a certain structure, a case of simply expressing "above" includes both a case of disposing the other structure immediately above the certain structure so as to contact the certain structure and a case of disposing the other structure above the certain structure with still another structure interposed therebetween, unless otherwise specified.

First Embodiment

Detection Device

Figure 2:
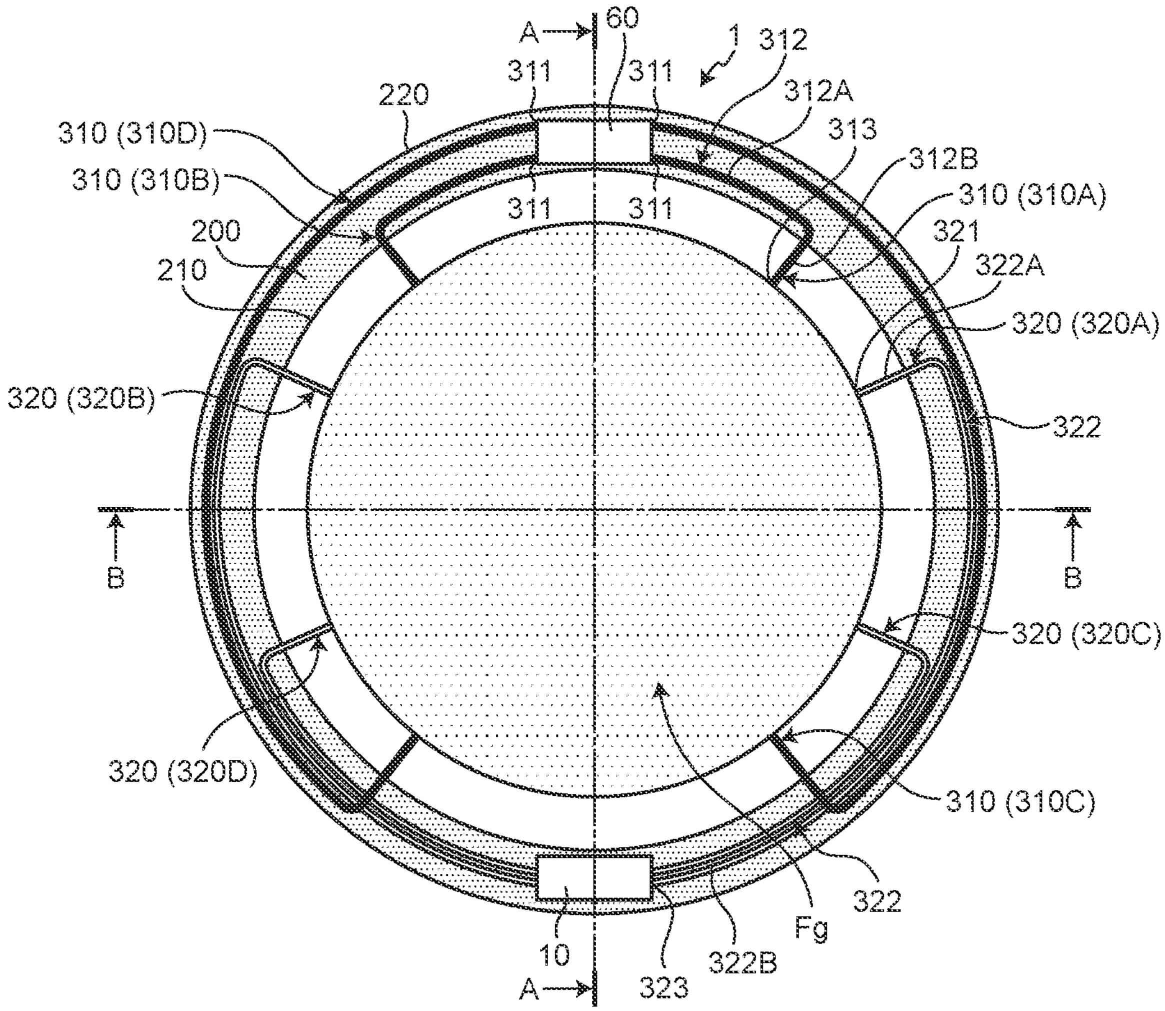
FIG. 2 is a schematic sectional view along section C-C illustrated in FIG. 1.
Figure 3:
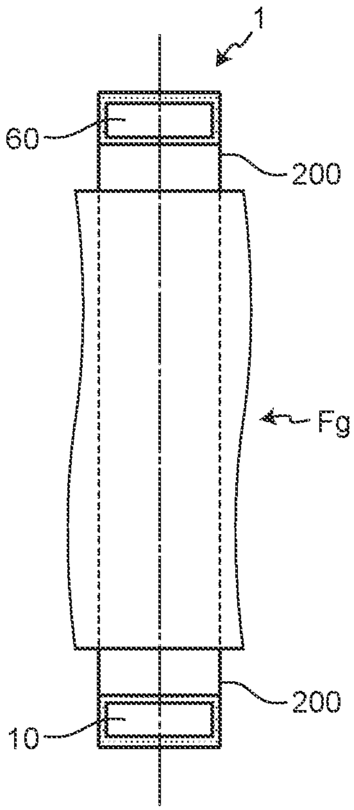
FIG. 3 is a schematic sectional view along section A-A illustrated in FIG. 2.
Figure 4:
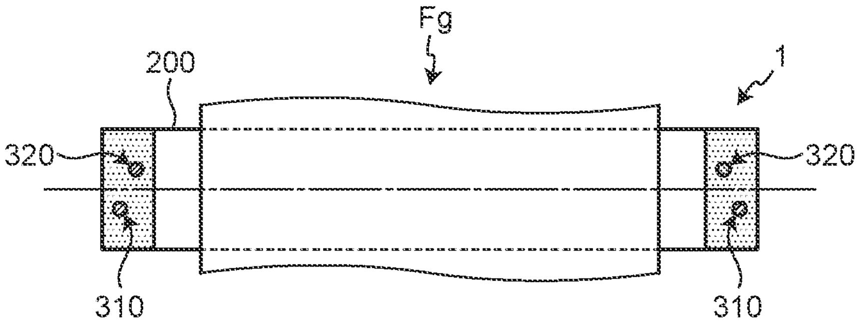
FIG. 4 is a schematic sectional view along section B-B illustrated in FIG. 2.
Figure 5:
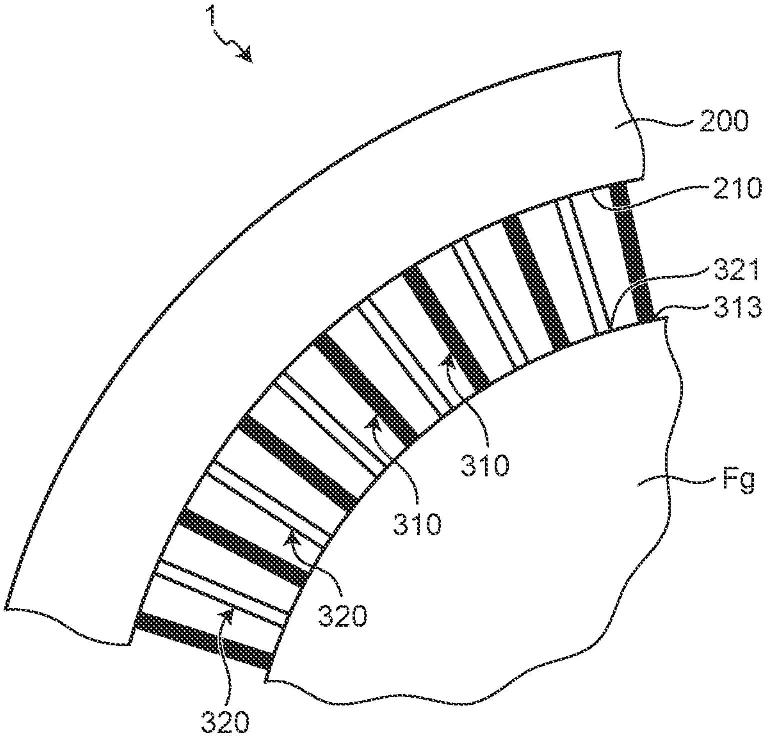
FIG. 5 is a partially enlarged schematic view of the detection device illustrated in FIG. 1, as viewed from a fingertip.

FIG. 1 is a schematic view illustrating an example of an external view of a state where a finger is accommodated in a detection device according to a first embodiment, as viewed from a lateral side of a housing. FIG. 2 is a schematic sectional view along section C-C illustrated in FIG. 1. FIG. 3 is a schematic sectional view along section A-A illustrated in FIG. 2. FIG. 4 is a schematic sectional view along section B-B illustrated in FIG. 2. FIG. 5 is a partially enlarged schematic view of the detection device illustrated in FIG. 1, as viewed from a fingertip.

A detection device 1 illustrated in FIGS. 1 and 2 is a finger ring-shaped device that can be worn on and removed from a human body, and is worn on a finger Fg of the human body. The term "finger Fg" includes, for example, a thumb, an index finger, a middle finger, a ring finger, and a little finger. The human body is that of a person to be authenticated whose identity is checked by the detection device 1. The detection device 1 can detect biometric information on a living body from the finger Fg wearing the detection device 1. The finger Fg is an example of a measurement target. The measurement target is the living body or a part of the living body, and is an object to be measured.

As illustrated in FIG. 2, the detection device 1 includes a housing 200, a light source 60, an optical sensor 10, a plurality of first light guides 310, and a plurality of second light guides 320. The detection device 1 is a device that includes a battery (not illustrated) in the housing 200, and is operated by power of the battery. In FIG. 2, to simplify the description, the numbers of the first light guides 310 and the second light guides 320 are reduced from the actual numbers.

The housing 200 is formed in a ring shape (annular shape) that can be worn on the finger Fg, and is a wearing member to be worn on the living body. The housing 200 is formed of a housing material, such as a non-translucent or translucent resin material. The housing 200 accommodates therein the light source 60 and the optical sensor 10, and accommodates the first light guides 310 and the second light guides 320 so as to project from the interior of the housing 200 toward the finger Fg. In the present embodiment, as illustrated in FIGS. 2 and 3, a case will be described where the light source 60 and the optical sensor 10 are arranged so as to face each other in positions apart from each other on one side and the other side of the housing 200. However, the arrangement is not limited to this arrangement. The light source 60 and the optical sensor 10 may be arranged closer to each other in the housing 200.

As illustrated in FIG. 4, the first light guides 310 and the second light guides 320 are arranged in the housing 200 so as to guide light emitted from the light source 60 to the optical sensor 10. The first light guides 310 that receive and guide the light emitted from the light source 60 are arranged in the housing 200. The second light guides 320 that guide the received light to the optical sensor 10 are arranged in the housing 200.

As illustrated in FIG. 2, a light-emitting portion 313 of each of the first light guides 310 and a light-receiving portion 321 of each of the second light guides 320 project from an inner peripheral surface 210 of the housing 200 toward inside the housing 200. The inner peripheral surface 210 is a surface to which the finger Fg located inside the housing 200 is located close. The housing 200 accommodates the first light guides 310 and the second light guides 320 between the inner peripheral surface 210 and an outer peripheral surface 220. The outer peripheral surface 220 is a surface of the housing 200 facing the inner peripheral surface 210. The housing 200 projects the light-emitting portions 313 and the light-receiving portions 321 from different positions of the inner peripheral surface 210 so that the light-emitting portions 313 of the first light guides 310 and the light-receiving portions 321 of the second light guides 320 make point contact with the finger Fg. The point contact means that the distal ends of the light-emitting portions 313 and the light-receiving portions 321 contact the finger Fg (measurement target) at points.

In the present embodiment, to simplify the description, a configuration of the detection device 1 will be described in which the housing 200 accommodates four of the first light guides 310 and four of the second light guides 320. However, the housing 200 is not limited to this configuration. As illustrated in FIG. 5, the housing 200 can accommodate therein the first light guides 310 and the second light guides 320, and project the light-emitting portions 313 of the first light guides 310 and the light-receiving portions 321 of the second light guides 320 from the inner peripheral surface 210 of the housing 200. That is, by projecting the light-emitting portions 313 of the first light guides 310 and the light-receiving portions 321 of the second light guides 320 from the inner peripheral surface 210 of the housing 200 in a manner similar to bristles of a brush, the detection device 1 can cause the distal ends of the light guides to make point contact with the finger Fg so as to improve the wearability when the detection device 1 is worn.

The detection device 1 may be provided with the light-emitting portions 313 of the first light guides 310 and the light-receiving portions 321 of the second light guides 320 on the entire surface of the inner peripheral surface 210 of the housing 200, or in a limited area. The limited area includes, for example, a partial area of the inner peripheral surface 210 of the housing 200 that is in contact with a portion of the finger Fg, such as a finger pulp, or a finger dorsum. One example illustrated in FIG. 5 illustrates a case of alternately arranging the first light guides 310 and the second light guides 320 of the detection device 1. However, the detection device 1 is not limited to this case. For example, the first light guides 310 and the second light guides 320 of the detection device 1 may be irregularly arranged instead of being alternately arranged. For example, the ratio between the numbers of the first light guides 310 and the second light guides 320 of the detection device 1 can be set to any ratio according to the specifications or the like of the device. For example, in the detection device 1, the second light guides 320 may be arranged near one first light guide 310 that emits light. In the present embodiment, in the detection device 1, the portions of the first light guides 310 and the second light guides 320 projecting from the housing 200 have the same length, but may have different lengths.

As illustrated in FIG. 2, the light source 60 is provided in the housing 200, and is capable of emitting the light to light-receiving portions 311 of the first light guides 310. For example, an inorganic light-emitting diode (LED) or an organic electroluminescent (EL) diode (organic light-emitting diode (OLED)) is used as the light source 60. The light source 60 emits light having a predetermined wavelength. In the present embodiment, the light source 60 emits near-infrared light, red light, and the like.

The reflected light of the near-infrared light contains information for detecting a vascular pattern. Red blood cells included in blood contain hemoglobin. The near-infrared light emitted from the light source 60 is easily absorbed by hemoglobin. In other words, the absorption coefficient of near-infrared light by hemoglobin is higher than that by other parts of the body. Therefore, the vascular pattern of veins or the like can be detected by reading the amount of light received by a plurality of photodiodes PD and identifying locations where the amount of the infrared light received is relatively smaller.

The reflected light of the near-infrared light and the red light contains information for measuring the oxygen saturation level in the blood (hereinafter, called "blood oxygen saturation level" ($SpO_2$)). The blood oxygen saturation level ($SpO_2$) refers to a ratio of an amount of oxygen actually bound to hemoglobin to the total amount of oxygen under the assumption that the oxygen is bound to all the hemoglobin in the blood.

The near-infrared light can be easily absorbed by hemoglobin. As the amount of hemoglobin increases, the amount of absorbed near-infrared light increases, and the amount of light received by the photodiodes PD decreases. That is, the total amount of hemoglobin is obtained from the amount of the received reflected light of the near-infrared light.

The hemoglobin has a dark red color when not bound to oxygen, and has a bright red color when bound to oxygen. Therefore, the absorption coefficient of the hemoglobin for absorbing the red light differs between when the hemoglobin is bound to oxygen and when the hemoglobin is not bound to oxygen. As a result, the amount of the reflected light of the red light increases as the hemoglobin bound to oxygen increases in the blood. In contrast, the amount of the reflected light of the red light decreases as the hemoglobin not bound to oxygen increases in the blood. Thus, the amount of the hemoglobin bound to oxygen is relatively obtained based on the amount of the received reflected light of the red light.

Then, by comparing the obtained total amount of the hemoglobin with the amount of the hemoglobin bound to oxygen, the ratio of the amount of oxygen actually bound to the hemoglobin (blood oxygen saturation level ($SpO_2$)) can be obtained. Thus, the detection device 1 can detect the biometric information on the living body in the finger Fg or the like by guiding the light emitted by the light source 60 to various positions on the inner peripheral surface 210 of the housing 200 through the first light guides 310, irradiating the measurement target, and detecting the light.

In the present disclosure, the light emitted from the light source 60 is not limited to the above-described light. The light source 60 may emit only near-infrared light having a wavelength of from 800 nm to smaller than 1000 nm, or red light having a wavelength of from 600 nm to smaller than 800 nm.

Figure 6:
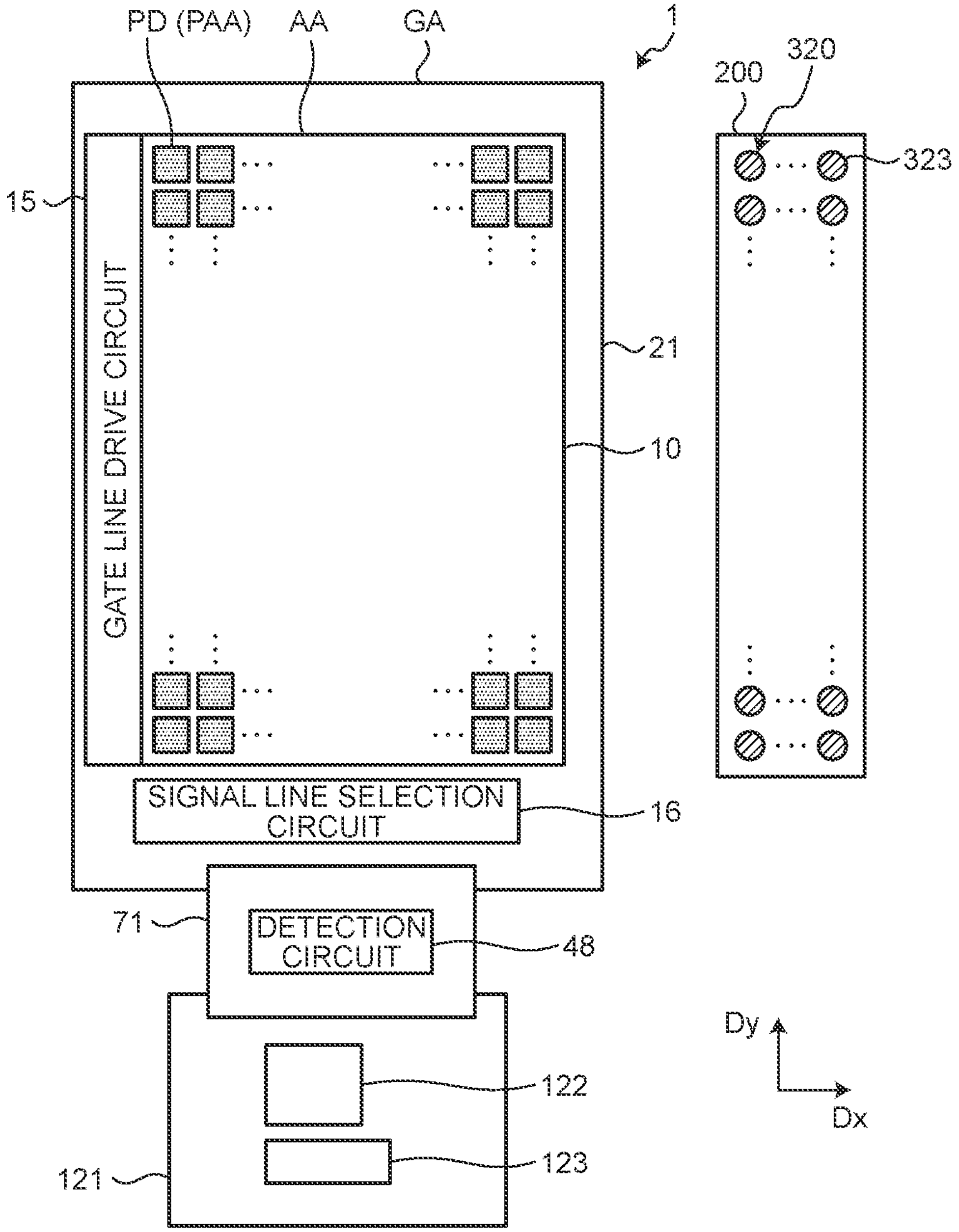
FIG. 6 is a configuration diagram illustrating an exemplary relation between first light guides and an optical sensor of the detection device according to the first embodiment.

The optical sensor 10 is provided in the housing 200, and detects the light guided by the second light guides 320. FIG. 6 is a configuration diagram illustrating an exemplary relation between the first light guides 310 and the optical sensor 10 of the detection device 1 according to the first embodiment. As illustrated in FIG. 6, the optical sensor 10 is an optical sensor that includes the photodiodes PD serving as photoelectric conversion elements. Each of the photodiodes PD included in the optical sensor 10 outputs an electrical signal corresponding to the light irradiating the photodiode PD as a detection signal Vdet to a signal line selection circuit 16. The optical sensor 10 perform the detection in response to a gate drive signal Vgcl supplied from a gate line drive circuit 15.

In one example illustrated in FIG. 6, the optical sensor 10 includes a sensor substrate 21. Each of the second light guides 320 has a light-emitting portion 323 located in the housing 200 so as to emit the guided light toward a corresponding one of the photodiodes PD. The light-emitting portion 323 is an end of the second light guide 320 that externally emits the guided light.

Figure 7:
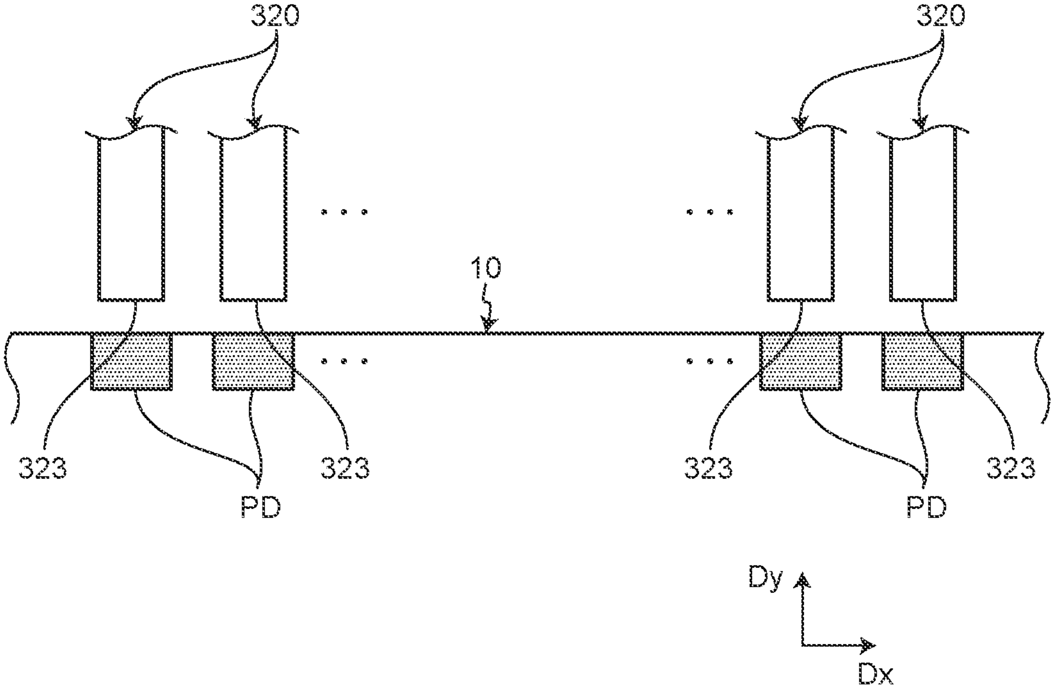
FIG. 7 is an enlarged schematic sectional view illustrating an exemplary arrangement of second light guides and photodiodes according to the first embodiment.

FIG. 7 is an enlarged schematic sectional view illustrating an exemplary arrangement of the second light guides 320 and the photodiodes PD according to the first embodiment. In one example illustrated in FIG. 7, each of the second light guides 320 is provided so as to face a corresponding one of the photodiodes PD on a one-to-one basis. The second light guides 320 are arranged in the housing 200 so as to emit the guided light from each of the light-emitting portions 323 toward the facing photodiode PD. In the detection device 1, optical members such as lenses condensing the light emitted from the light-emitting portions 323 to the photodiodes PD may be arranged between the second light guides 320 and the photodiodes PD.

In the present embodiment, the case is described where each of the second light guides 320 is provided so as to face a corresponding one of the photodiodes PD on a one-to-one basis. However, the configuration is not limited to this case. For example, one second light guide 320 may be configured to irradiate light from the light-emitting portion 323 toward a plurality of the photodiodes PD. In FIG. 2 explained above, to simplify the description, the number of the light-emitting portions 323 of the second light guides 320 is reduced from the actual numbers.

The sensor substrate 21 is electrically coupled to a control substrate 121 through a flexible printed circuit board 71. The flexible printed circuit board 71 is provided with a detection circuit 48. The control substrate 121 is provided with a control circuit 122 and a power supply circuit 123. The control circuit 122 is, for example, a field-programmable gate array (FPGA). The control circuit 122 supplies control signals to the optical sensor 10, the gate line drive circuit 15, and the signal line selection circuit 16 to control the detection operation of the optical sensor 10. The control circuit 122 supplies a control signal to the light source 60 to control lighting or non-lighting of the light source 60. The power supply circuit 123 supplies voltage signals including, for example, a sensor power supply signal VDDSNS (refer to FIG. 10) to the optical sensor 10, the gate line drive circuit 15, and the signal line selection circuit 16. The power supply circuit 123 supplies a power supply voltage to the light source 60.

The sensor substrate 21 has a detection area AA and a peripheral area GA. The detection area AA is an area provided with the photodiodes PD included in the optical sensor 10. The peripheral area GA is an area between the outer perimeter of the detection area AA and the ends of the sensor substrate 21, and is an area not overlapping the photodiodes PD.

The gate line drive circuit 15 and the signal line selection circuit 16 are provided in the peripheral area GA. Specifically, the gate line drive circuit 15 is provided in an area extending along a second direction Dy in the peripheral area GA. The signal line selection circuit 16 is provided in an area extending along a first direction Dx in the peripheral area GA, and is provided between the optical sensor 10 and the detection circuit 48.

The first direction Dx is one direction in a plane parallel to the sensor substrate 21. The second direction Dy is one direction in the plane parallel to the sensor substrate 21, and is a direction orthogonal to the first direction Dx. The second direction Dy may non-orthogonally intersect the first direction Dx. A third direction Dz is a direction orthogonal to the first direction Dx and the second direction Dy, and is a direction normal to the sensor substrate 21.

Figure 8:
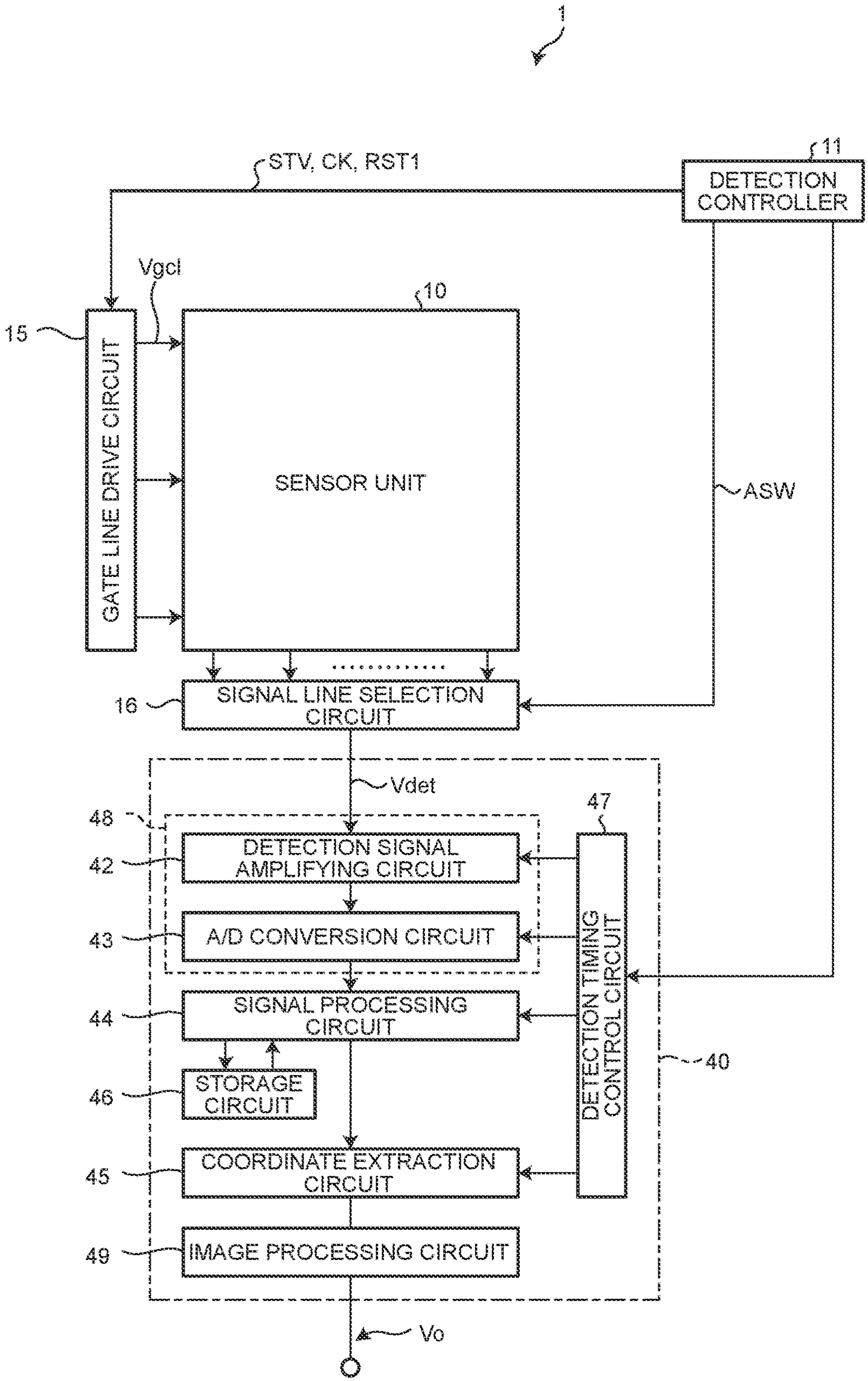
FIG. 8 is a block diagram illustrating a configuration example of the detection device according to the first embodiment.

FIG. 8 is a block diagram illustrating a configuration example of the detection device 1 according to the first embodiment. As illustrated in FIG. 8, the detection device 1 further includes a detection controller (a detection control circuit) 11 and a detector 40 (a detection processing circuit). The control circuit 122 includes one, some, or all functions of the detection controller 11. The control circuit 122 also includes one, some, or all functions of the detector 40 other than those of the detection circuit 48.

The detection controller 11 is a circuit that supplies respective control signals to the gate line drive circuit 15, the signal line selection circuit 16, and the detector 40 to control operations thereof. The detection controller 11 supplies various control signals including, for example, a start signal STV, a clock signal CK, and a reset signal RST1 to the gate line drive circuit 15. The detection controller 11 also supplies various control signals including, for example, a selection signal ASW to the signal line selection circuit 16. The detection controller 11 supplies various control signals to the light source 60 to control the lighting and the non-lighting of the light source 60.

The gate line drive circuit 15 is a circuit that drives a plurality of gate lines GCL (refer to FIG. 9) based on the various control signals. The gate line drive circuit 15 sequentially or simultaneously selects the gate lines GCL, and supplies the gate drive signals Vgcl to the selected gate lines GCL. Through this operation, the gate line drive circuit 15 selects the photodiodes PD coupled to the gate lines GCL.

Figure 10:
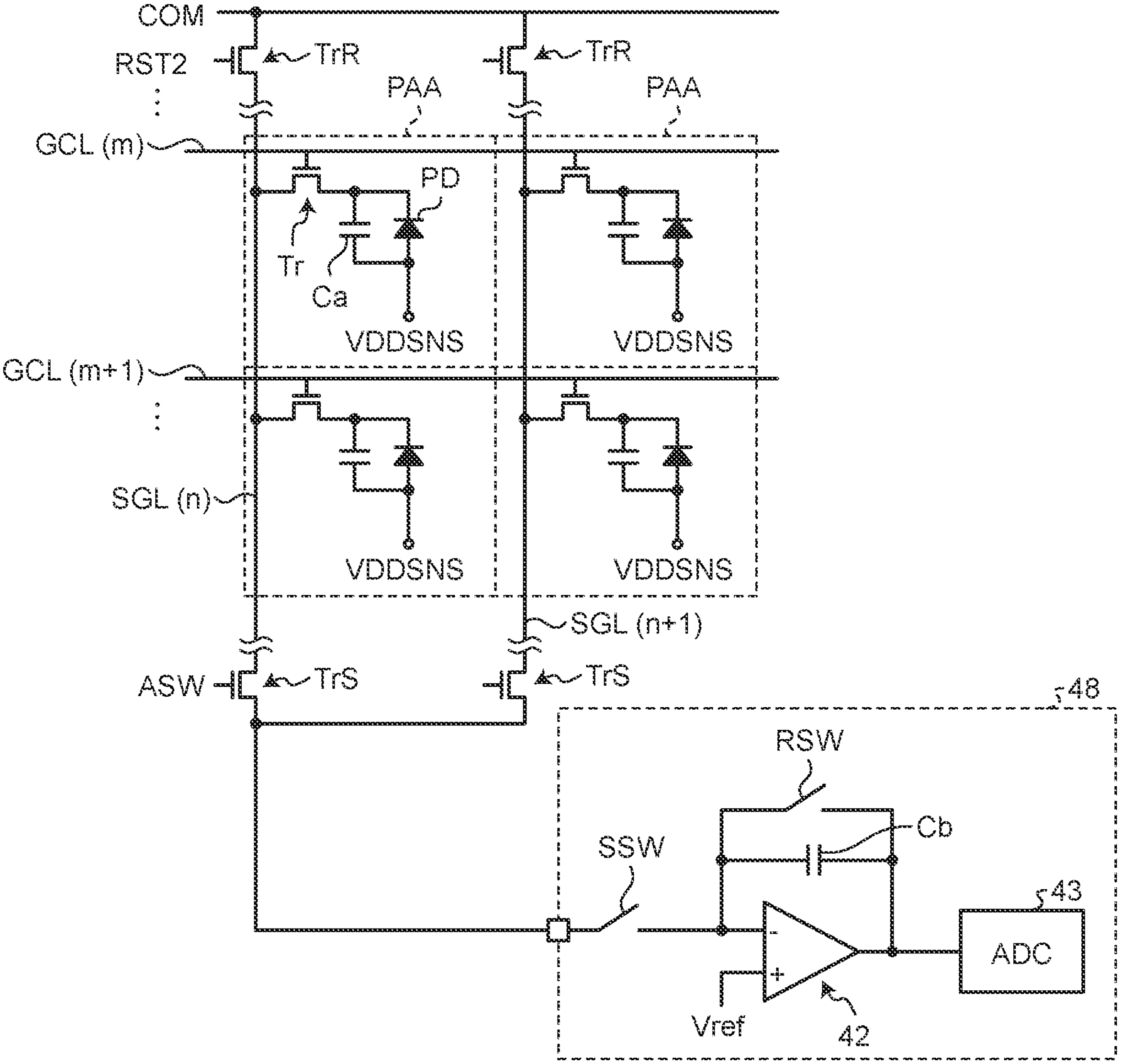
FIG. 10 is a circuit diagram illustrating a plurality of partial detection areas.

The signal line selection circuit 16 is a switch circuit that sequentially or simultaneously selects a plurality of signal lines SGL (refer to FIG. 10). The signal line selection circuit 16 is, for example, a multiplexer. The signal line selection circuit 16 couples the selected signal lines SGL to the detection circuit 48 based on the selection signal ASW supplied from the detection controller 11. Through this operation, the signal line selection circuit 16 outputs the detection signals Vdet of the photodiodes PD to the detector 40.

The detector 40 includes the detection circuit 48, a signal processing circuit 44, a coordinate extraction circuit 45, a storage circuit 46, a detection timing control circuit 47, and an image processing circuit 49. The detection timing control circuit 47 performs control to cause the detection circuit 48, the signal processing circuit 44, the coordinate extraction circuit 45, and the image processing circuit 49 to operate in synchronization with one another based on a control signal supplied from the detection controller 11.

The detection circuit 48 is, for example, an analog front-end (AFE) circuit. The detection circuit 48 is a signal processing circuit having functions of at least a detection signal amplifying circuit 42 and an analog-to-digital (A/D) conversion circuit 43. The detection signal amplifying circuit 42 amplifies the detection signals Vdet. The A/D conversion circuit 43 converts analog signals output from the detection signal amplifying circuit 42 into digital signals.

The signal processing circuit 44 is a logic circuit that detects a predetermined physical quantity received by the optical sensor 10 based on output signals of the detection circuit 48. The signal processing circuit 44 can detect asperities on a biological surface of the finger Fg or a palm based on the signals from the detection circuit 48 when the finger Fg is in contact with or in proximity to a detection surface. The signal processing circuit 44 can detect the information on the living body based on the signals from the detection circuit 48. Examples of the information on the living body include pulsation and the blood oxygen saturation level of the finger Fg.

The signal processing circuit 44 may also perform processing of acquiring the detection signals Vdet (information on the living body) simultaneously detected by the photodiodes PD, and averaging the detection signals Vdet. In this case, the detector 40 can perform stable detection by reducing measurement errors caused by noise and/or relative positional misalignment between the object to be detected, such as the finger Fg, and the optical sensor 10.

The storage circuit 46 temporarily stores therein signals calculated by the signal processing circuit 44. The storage circuit 46 may be, for example, a random-access memory (RAM) or a register circuit.

The coordinate extraction circuit 45 is a logic circuit that obtains detected coordinates of the asperities on the biological surface of the finger or the like when the contact or the proximity of the finger is detected by the signal processing circuit 44. The coordinate extraction circuit 45 is the logic circuit that also obtains detected coordinates of blood vessels of the finger Fg or the palm. The image processing circuit 49 combines the detection signals Vdet output from the respective photodiodes PD of the optical sensor 10 to generate two-dimensional information representing the shape of the asperities on the biological surface of the finger Fg or the like and two-dimensional information representing the shape of the blood vessels of the finger Fg or the palm. The coordinate extraction circuit 45 may output the detection signals Vdet as sensor outputs Vo instead of calculating the detected coordinates. A case can be considered where the detector 40 does not include the coordinate extraction circuit 45 and the image processing circuit 49.

The detection controller 11 has a function to compare the detected information on the living body with authentication information stored in advance and authenticate the person to be authenticated based on the result of the comparison. The detection controller 11 has a function to control transmission of the detected information on the living body to an external device through a communication device (not illustrated in the drawings).

Figure 9:
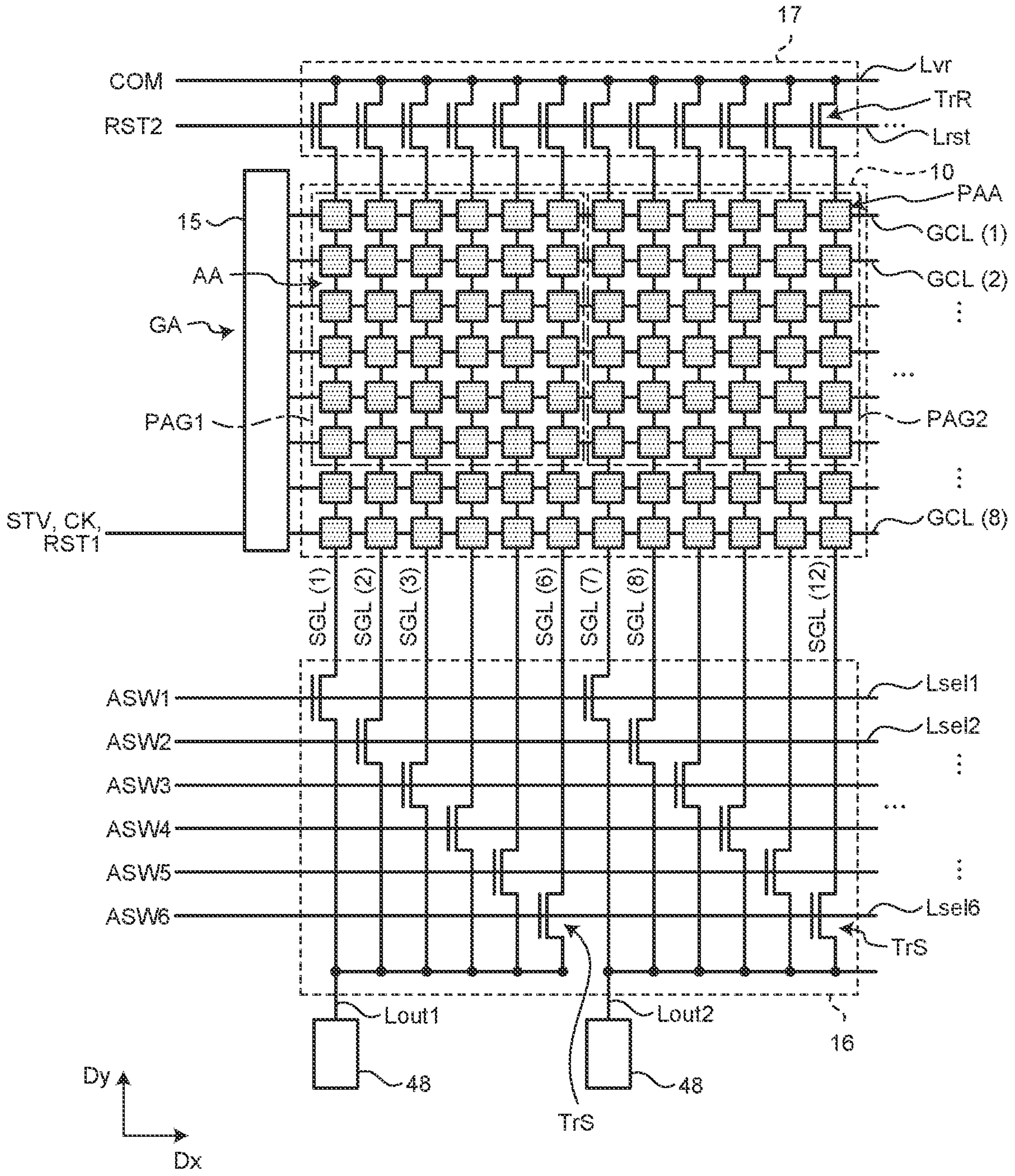
FIG. 9 is a circuit diagram illustrating the detection device.

The following describes a circuit configuration example of the detection device 1. FIG. 9 is a circuit diagram illustrating the detection device 1. FIG. 10 is a circuit diagram illustrating a plurality of partial detection areas. FIG. 10 also illustrates a circuit configuration of the detection circuit 48.

As illustrated in FIG. 9, the optical sensor 10 has a plurality of partial detection areas PAA arranged in a matrix having a row-column configuration. Each of the partial detection areas PAA is provided with the photodiode PD.

The gate lines GCL extend in the first direction Dx, and are each coupled to the partial detection areas PAA arranged in the first direction Dx. A plurality of gate lines GCL(1), GCL(2), . . . , GCL(8) are arranged in the second direction Dy, and are each coupled to the gate line drive circuit 15. In the following description, the gate lines GCL(1), GCL(2), . . . , GCL(8) will each be simply referred to as the gate line GCL when need not be distinguished from one another. For ease of understanding of the description, FIG. 10 illustrates eight of the gate lines GCL. However, this is merely an example, and M (where M is eight or larger, and is, for example, equal to 256) of the gate lines GCL may be arranged.

The signal lines SGL extend in the second direction Dy, and are each coupled to the photodiodes PD of the partial detection areas PAA arranged in the second direction Dy. A plurality of signal lines SGL(1), SGL(2), . . . , SGL(12) are arranged in the first direction Dx, and are each coupled to the signal line selection circuit 16 and a reset circuit 17. In the following description, the signal lines SGL(1), SGL(2), . . . , SGL(12) will each be simply referred to as the signal line SGL when need not be distinguished from one another.

For ease of understanding of the description, 12 of the signal lines SGL are illustrated. However, this is merely an example, and N (where N is 12 or larger, and is, for example, equal to 252) of the signal lines SGL may be arranged. In FIG. 6, the optical sensor 10 is provided between the signal line selection circuit 16 and the reset circuit 17. The present disclosure is not limited thereto. The signal line selection circuit 16 and the reset circuit 17 may be coupled to ends of the signal lines SGL in the same direction.

The gate line drive circuit 15 receives the various control signals such as the start signal STV, the clock signal CK, and the reset signal RST1 from the control circuit 122 (refer to FIG. 6). The gate line drive circuit 15 sequentially selects the gate lines GCL(1), GCL(2), . . . , GCL(8) in a time-division manner based on the various control signals. The gate line drive circuit 15 supplies the gate drive signal Vgcl to the selected one of the gate lines GCL. This operation supplies the gate drive signal Vgcl to a plurality of first switching elements Tr coupled to the gate line GCL, and corresponding ones of the partial detection areas PAA arranged in the first direction Dx are selected as detection targets.

The gate line drive circuit 15 may perform different driving for each of detection modes including detection of a fingerprint and detection of a plurality of different items of information on the living body (including, for example, the pulsation and the blood oxygen saturation level). For example, the gate line drive circuit 15 may drive more than one of the gate lines GCL in a bundle.

Specifically, the gate line drive circuit 15 simultaneously selects a predetermined number of the gate lines GCL from among the gate lines GCL(1), GCL(2), . . . , GCL(8) based on the control signals. For example, the gate line drive circuit 15 simultaneously selects six of the gate lines GCL (1) to GCL(6), and supplies thereto the gate drive signals Vgcl. The gate line drive circuit 15 supplies the gate drive signals Vgcl through the selected six gate lines GCL to the first switching elements Tr. Through this operation, detection area groups PAG1 and PAG2 each including corresponding ones of the partial detection areas PAA arranged in the first direction Dx and the second direction Dy are selected as the respective detection targets. The gate line drive circuit 15 drives the predetermined number of the gate lines GCL in a bundle, and sequentially supplies the gate drive signals Vgcl to each unit of the predetermined number of the gate lines GCL.

The signal line selection circuit 16 includes a plurality of selection signal lines Lsel, a plurality of output signal lines Lout, and third switching elements TrS. The third switching elements TrS are provided correspondingly to the respective signal lines SGL. Six of the signal lines SGL(1), SGL(2), . . . , SGL(6) are coupled to a common output signal line Lout1. Six of the signal lines SGL(7), SGL(8), . . . , SGL(12) are coupled to a common output signal line Lout2. The output signal lines Lout1 and Lout2 are each coupled to the detection circuit 48.

The signal lines SGL(1), SGL(2), . . . , SGL(6) are grouped into a first signal line block, and the signal lines SGL(7), SGL(8), . . . , SGL(12) are grouped into a second signal line block. The selection signal lines Lsel are coupled to the gates of the respective third switching elements TrS included in one of the signal line blocks. One of the selection signal lines Lsel is coupled to the gates of the third switching elements TrS in the signal line blocks.

Specifically, selection signal lines Lsel1, Lsel2, . . . , Lsel6 are coupled to the third switching elements TrS corresponding to the signal lines SGL(1), SGL(2), . . . , SGL(6), respectively. The selection signal line Lsel1 is coupled to one of the third switching elements TrS corresponding to the signal line SGL(1) and one of the third switching elements TrS corresponding to the signal line SGL(7). The selection signal line Lsel2 is coupled to one of the third switching elements TrS corresponding to the signal line SGL(2) and one of the third switching elements TrS corresponding to the signal line SGL(8).

The control circuit 122 (refer to FIG. 6) sequentially supplies the selection signal ASW to the selection signal lines Lsel. This operation causes the signal line selection circuit 16 to operate the third switching elements TrS to sequentially select the signal lines SGL in one of the signal line blocks in a time-division manner. The signal line selection circuit 16 selects one of the signal lines SGL in each of the signal line blocks. With the above-described configuration, the detection device 1 can reduce the number of integrated circuits (ICs) including the detection circuit 48 or the number of terminals of the ICs.

The signal line selection circuit 16 may couple more than one of the signal lines SGL in a bundle to the detection circuit 48. Specifically, the control circuit 122 (refer to FIG. 6) simultaneously supplies the selection signal ASW to the selection signal lines Lsel. This operation causes the signal line selection circuit 16 to operate the third switching elements TrS to select the signal lines SGL (for example, six of the signal lines SGL) in one of the signal line blocks, and couple the selected signal lines SGL to the detection circuit 48. As a result, the signals detected in each of the detection area groups PAG1 and PAG2 are output to the detection circuit 48. In this case, the signals from the partial detection areas PAA (photodiodes PD) included in each of the detection area groups PAG1 and PAG2 are integrated and output to the detection circuit 48.

By operating the gate line drive circuit 15 and the signal line selection circuit 16 to perform the detection for each of the detection area groups PAG1 and PAG2, the strength of the detection signal Vdet obtained by a one-time detection operation is improved, so that the sensor sensitivity can be improved. The time required for the detection can also be reduced. As a result, the detection device 1 can repeatedly perform the detection in a short time, and thus, can improve the signal-to-noise ratio (S/N), and can also accurately detect a temporal change in the information on the living body, such as a pulse wave.

As illustrated in FIG. 9, the reset circuit 17 includes a reference signal line Lvr, a reset signal line Lrst, and fourth switching elements TrR. The fourth switching elements TrR are provided correspondingly to the signal lines SGL. The reference signal line Lvr is coupled to either the sources or the drains of the fourth switching elements TrR. The reset signal line Lrst is coupled to the gates of the fourth switching elements TrR.

The control circuit 122 supplies a reset signal RST2 to the reset signal line Lrst. This operation turns on the fourth switching elements TrR to electrically couple the signal lines SGL to the reference signal line Lvr. The power supply circuit 123 supplies a reference signal COM to the reference signal line Lvr. This operation supplies the reference signal COM to a capacitive element Ca (refer to FIG. 10) included in each of the partial detection areas PAA.

As illustrated in FIG. 10, each of the partial detection areas PAA includes the photodiode PD, the capacitive element Ca, and a corresponding one of the first switching elements Tr. FIG. 10 illustrates two gate lines GCL(m) and GCL(m+1) arranged in the second direction Dy among the gate lines GCL. FIG. 10 also illustrates two signal lines SGL(n) and SGL(n+1) arranged in the first direction Dx among the signal lines SGL. The partial detection area PAA is an area surrounded by the gate lines GCL and the signal lines SGL. Each of the first switching elements Tr is provided correspondingly to the photodiode PD. The first switching element Tr is constituted by a thin-film transistor, and in this example, constituted by an n-channel metal oxide semiconductor (MOS) thin-film transistor (TFT).

The gates of the first switching elements Tr belonging to the partial detection areas PAA arranged in the first direction Dx are coupled to the gate line GCL. The sources of the first switching elements Tr belonging to the partial detection areas PAA arranged in the second direction Dy are coupled to the signal line SGL. The drain of the first switching element Tr is coupled to the cathode of the photodiode PD and the capacitive element Ca.

The anode of the photodiode PD is supplied with the sensor power supply signal VDDSNS from the power supply circuit 123. The signal line SGL and the capacitive element Ca are supplied with the reference signal COM that serves as an initial potential of the signal line SGL and the capacitive element Ca from the power supply circuit 123.

When the partial detection area PAA is irradiated with light, a current corresponding to the amount of the light flows through the photodiode PD. As a result, an electric charge is stored in the capacitive element Ca. After the first switching element Tr is turned on, a current corresponding to the electric charge stored in the capacitive element Ca flows through the signal line SGL. The signal line SGL is coupled to the detection circuit 48 through a corresponding one of the third switching elements TrS of the signal line selection circuit 16. Thus, the detection device 1 can detect a signal corresponding to the amount of the light irradiating the photodiode PD in each of the partial detection areas PAA or signals corresponding to the amounts of the light irradiating the photodiodes PD in each of the detection area groups PAG1 and PAG2.

During a read period, a switch SSW of the detection circuit 48 is turned on, and the detection circuit 48 is coupled to the signal lines SGL. The detection signal amplifying circuit 42 of the detection circuit 48 converts a current supplied from the signal lines SGL into a voltage corresponding to a value of the current, and amplifies the result. A reference voltage Vref having a fixed potential is supplied to a non-inverting input portion (+) of the detection signal amplifying circuit 42, and the signal lines SGL are coupled to an inverting input terminal (−) of the detection signal amplifying circuit 42. In the present embodiment, the same signal as the reference signal COM is supplied as the reference voltage Vref. The detection signal amplifying circuit 42 includes a capacitive element Cb and a reset switch RSW. During a reset period, the reset switch RSW is turned on, and the electric charge of the capacitive element Cb is reset.

With the above-described configuration, the detection device 1 including the photodiodes PD can detect the information on the living body, such as a vein pattern of the finger Fg, a dermatoglyphic pattern, the blood oxygen saturation level, and the pulsation, and supply the biometric information including the detected information to outside the device.

As illustrated in FIG. 2, the detection device 1 includes the line-shaped first light guides 310 having different lengths in the housing 200. The first light guide 310 is formed in a line shape capable of receiving the light emitted by the light source 60 and guiding the received light. In one example illustrated in FIG. 2, four first light guides 310A, 310B, 310C, and 310D of the detection device 1 are illustrated. The first light guides 310A and 310B are optical fibers having similar lengths and are members that each guide the light emitted by the light source 60 to a first distance. The first light guides 310C and 310D are formed to be longer than the first light guides 310A and 310B, and are optical fibers having similar lengths. The first light guides 310C and 310D are members that each guide the light emitted by the light source 60 to a second distance farther than the first distance. Hereinafter, when the first light guides 310A, 310B, 310C, and 310D are not distinguished from one another, they are each referred to as "first light guide 310".

A light-receiving side of the first light guide 310 faces the light source 60 so as to be capable of receiving the light emitted by the light source 60, and a light-emitting side of the first light guide 310 projects from inside the housing 200. In the example illustrated in FIG. 2, the first light guide 310 includes a light-receiving portion 311, a light-guiding portion 312, and the light-emitting portion 313. The light-receiving portion 311 is an end on the light-receiving side of the first light guide 310 provided in the housing 200, and receives the light emitted by the light source 60. The light-guiding portion 312 includes a body 312A embedded in the housing 200 and a projection 312B projecting from inside to outside the housing 200. The light-guiding portion 312 is bent between the body 312A and the projection 312B so as not to hinder the guiding of the light. The light-emitting portion 313 is an end on the light-emitting side of the first light guide 310 that irradiates the finger Fg or the like located inside the housing 200 with the light guided by the light-guiding portion 312. The light-emitting portion 313 is a portion where the first light guide 310 makes point contact with the finger Fg when the housing 200 is worn on the finger Fg, and emits the guided light toward the finger Fg.

The detection device 1 includes the line-shaped second light guides 320 having different lengths in the housing 200. The second light guide 320 is formed in a line shape capable of receiving the light emitted by the light-emitting portion 313 of the first light guide 310 and guiding the received light. In the example illustrated in FIG. 2, four second light guides 320A, 320B, 320C, and 320D of the detection device 1 are illustrated. The second light guides 320A and 320B are optical fibers having similar lengths and are members that guide the light emitted by the nearby light-emitting portions 313 of the first light guides 310 to the optical sensor 10. The second light guides 320C and 320D are formed to be shorter than the second light guides 320A and 320B, and are optical fibers having similar lengths. The second light guides 320C and 320D are members that guide the light emitted by the light-emitting portions 313 of the first light guides 310 closer to the optical sensor 10 than the second light guides 320A and 320B to the optical sensor 10. Hereinafter, when the second light guides 320A, 320B, 320C, and 320D are not distinguished from one another, they are each referred to as "second light guide 320".

The second light guide 320 is provided such that a light-receiving side thereof projects from inside to outside the housing 200, and a light-emitting side thereof faces the photodiode PD of the optical sensor 10. In the example illustrated in FIG. 2, the second light guide 320 includes the light-receiving portion 321, a light-guiding portion 322, and the light-emitting portion 323. The light-receiving portion 321 is an end on the light-receiving side of the second light guide 320 that projects out of the housing 200 and receives, for example, the light emitted by the light-emitting portion 313 of the first light guide 310. The light-receiving portion 321 is a portion where the second light guide 320 makes point contact with the finger Fg when the housing 200 is worn on the finger Fg, and receives, for example, light reflected by the finger Fg and the direct light emitted by the nearby light-emitting portion 313 of the first light guide 310. The light-guiding portion 322 includes a projection 322A projecting from inside to outside the housing 200 and a body 322B embedded in the housing 200. The light-guiding portion 322 is bent between the projection 322A and the body 322B so as not to hinder the guiding of the light. In the example illustrated in FIG. 2, the light-guiding portion 322 is illustrated so as to overlap the first light guide 310C, but is located in the housing 200 so as not to intersect the first light guide 310C. The light-emitting portion 323 is an end on the light-emitting side of the second light guide 320 that irradiates the optical sensor 10 with the light guided by the light-guiding portion 312. The light-emitting portion 323 irradiates predetermined one of the photodiodes PD of the optical sensor 10 with the light guided in the second light guide 320. That is, the light-emitting portion 323 can pin-pointedly irradiate a corresponding one of the photodiodes PD of the optical sensor 10 with the light received in an area on the inner peripheral surface 210 of the housing 200 where the light-receiving portion 321 projects. The light-emitting portion 323 may be configured to irradiate more than one of the photodiodes PD with light received in an area where the light-receiving portion 321 projects.

In the present embodiment, a plurality of light-receiving areas are set in a matrix having a row-column configuration corresponding to the detection area AA of the optical sensor 10 on the inner peripheral surface 210 of the housing 200 of the detection device 1, and the light-receiving portion 321 of one second light guide 320 projects in each of the light-receiving areas. The light-receiving areas of the housing 200 may occupy the entire area of the inner peripheral surface 210 of the housing 200, or a portion of the inner peripheral surface 210. This configuration allows the optical sensor 10 to detect the amount of light received by the photodiodes PD as information indicating an image in the detection area AA on the inner peripheral surface 210 of the housing 200.

Figure 11:
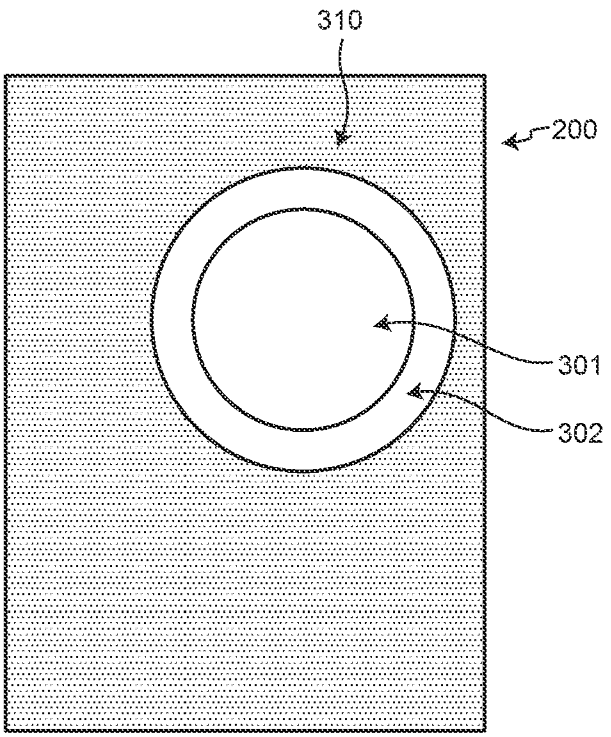
FIG. 11 is a schematic sectional view obtained by enlarging one of the first light guides of the detection device illustrated in FIG. 1.

FIG. 11 is a schematic sectional view obtained by enlarging the first light guide 310 of the detection device illustrated in FIG. 1. As illustrated in FIG. 11, the first light guide 310 uses an optical fiber including a transparent core 301 and cladding 302 formed around the core 301. In the first light guide 310, the refractive index of the cladding 302 on the outside is higher than that of the core 301 on the inside. Examples of the optical fiber include a quartz fiber, a multi-component glass optical fiber, and a plastic optical fiber. The second light guide 320 (not illustrated) uses an optical fiber having the same configuration as that of the first light guide 310. Thus, since the first light guides 310 and the second light guides 320 use the optical fibers, the detection device 1 is provided in the housing 200 in the state where the first light guides 310 and the second light guides 320 do not interfere with each other.

The above has described the configuration example of the detection device 1 according to the present embodiment. The configuration described above using FIGS. 1 to 11 is merely an example, and the configuration of the detection device 1 according to the present embodiment is not limited to the example. The configuration of the detection device 1 according to the present embodiment can be flexibly modified according to specifications and operations.

Detection Example of Detection Device Worn on Finger

The following describes a detection example of the detection device 1 worn on the finger Fg. As illustrated in FIG. 5, in the detection device 1, ends of the first light guides 310 and a second light guides 320 project in a brush-like manner from the inner peripheral surface 210 of the housing 200, and the finger Fg is inserted toward inside the housing 200. With this configuration, when the detection device 1 is worn on the finger Fg as illustrated in FIG. 1, the ends of the first light guides 310 and the second light guides 320 make point contact with the finger Fg as illustrated in FIG. 2.

The detection device 1 turns on the light source 60 at the time of detection while being worn on the finger Fg. The time of detection includes, for example, a predetermined date and time, and a time when the detection is instructed. In the detection device 1, the light-receiving portion 311 of each of the first light guides 310A, 310B, 310C, and 310D receives the light emitted by the light source 60 that is turned on. The detection device 1 emits the light guided through the light-guiding portion 312 by each of the first light guides 310A, 310B, 310C, and 310D from the light-emitting portion 313 toward the finger Fg. Through this operation, the detection device 1 can emit the light emitted by one light source 60 from the first light guides 310A, 310B, 310C, and 310D in different areas (projection positions) on the inner peripheral surface 210 of the housing 200.

The detection device 1 receives, for example, the light reflected by the finger Fg and the direct light at the light-receiving portions 321 of the second light guides 320A, 320B, 320C, and 320D, and guides the light in the light-guiding portions 322 toward the optical sensor 10. The detection device 1 emits the light guided through the light-guiding portion 322 by each of the light-guiding portions 322 of the second light guides 320A, 320B, 320C, 320D from the light-emitting portion 323 toward the optical sensor 10. The detection device 1 detects the biometric information on the finger Fg based on the amount of light detected by each of the photodiodes PD of the optical sensor 10, and stores the detected biometric information in, for example, the storage circuit 46.

As described above, when the detection device 1 is worn on the finger Fg, the light-emitting portions 313 of the first light guides 310 projecting from the housing 200 and in contact with the finger Fg irradiate the finger Fg, and the light received by the light-receiving portions 321 of the second light guides 320 projecting from the housing 200 is emitted to the optical sensor 10. This operation allows the detection device 1 to measure the light emitted from a plurality of locations of the housing 200 using one optical sensor 10. Therefore, the detection device 1 can improve the measurement accuracy of the biometric information. The detection device 1 can improve the irradiation area of the light source 60 in the housing 200 by guiding the light from the light source 60 using the first light guides 310 and emitting the light from different positions. As a result, the detection device 1 can measure the biometric information from a range where the first light guides 310 are in contact with the measurement target. Therefore, the measurement accuracy of the biometric information when the detection device 1 is worn on the measurement target can be improved. In addition, since the detection device 1 can be provided with as many irradiation positions in the housing 200 as the number of the first light guides 310, the number of the light sources 60 can be reduced to less than the number of the irradiation positions, thus being able to reduce the size of the device. When the detection device 1 is worn on the finger Fg, the ends of the first light guides 310 and the second light guides 320 projecting from the housing 200 make point contact with the finger Fg, which provides better touch and improved wearability.

Since the housing 200 is formed in the ring shape, simply wearing the detection device 1 on the finger Fg can cause the ends of the first light guides 310 and the second light guides 320 to make point contact with the finger Fg so as to surround the surface of the finger Fg. As a result, the detection device 1 can reduce the physical restraint on the person to be authenticated, and can also improve the wearability.

Method for Manufacturing Detection Device

Figure 12:
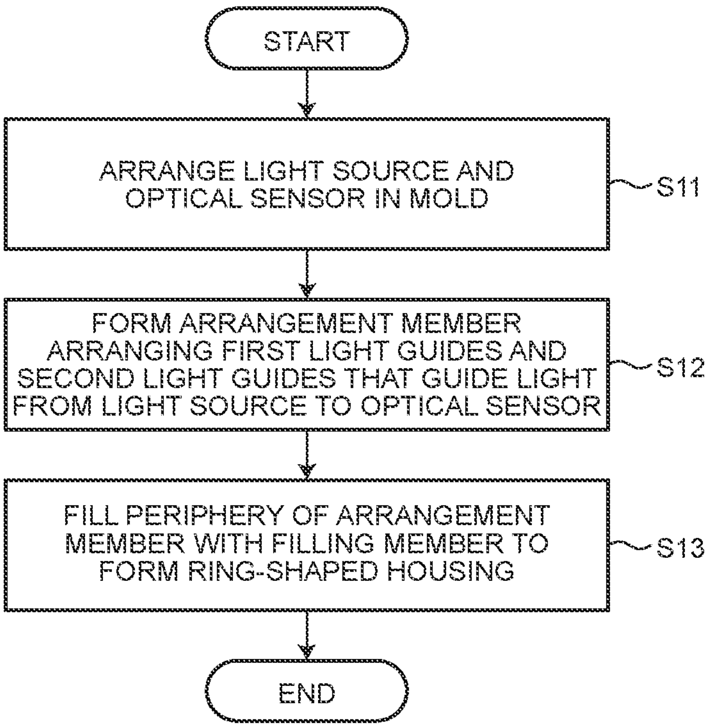
FIG. 12 is a flowchart illustrating an exemplary method for manufacturing the detection device according to the first embodiment.
Figure 13:
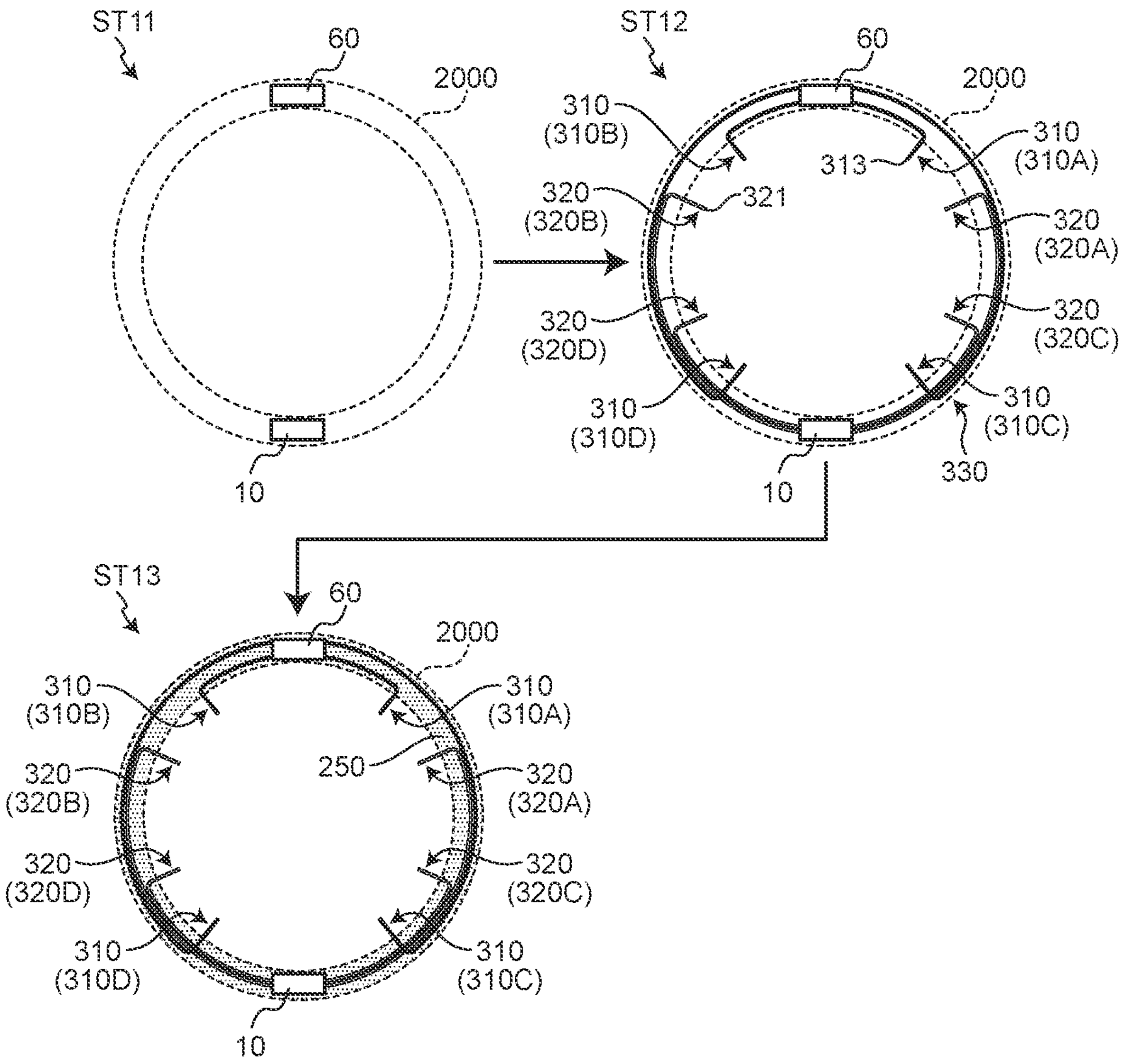
FIG. 13 is a diagram for explaining processes of the manufacturing method illustrated in FIG. 12.

FIG. 12 is a flowchart illustrating an exemplary method for manufacturing the detection device 1 according to the first embodiment. FIG. 13 is a diagram for explaining processes of the manufacturing method illustrated in FIG. 12. In the example illustrated in FIG. 12, the manufacturing method includes the processes at Step S11, Step S12, and Step S13 for manufacturing the housing 200 of the detection device 1, and the processes are sequentially performed. To simplify the explanation, the manufacturing method illustrated in FIG. 12 illustrates only the method for manufacturing the light source 60, the optical sensor 10, and the first and the second light guides 310 and 320 that are accommodated in the housing 200.

Step S11 of the manufacturing method is a process of arranging the light source 60 and the optical sensor 10 in a mold 2000, as illustrated in Process ST11 in FIG. 13. The mold 2000 is a metal mold for forming the ring-shaped housing 200. In the present disclosure, the light source 60 and the optical sensor 10 are arranged in opposed positions of the mold 2000 at Step S11. After Step S11 ends, the manufacturing method proceeds to a process at Step S12.

As illustrated in Process ST12 in FIG. 13, Step S12 of the manufacturing method is a process of forming an arrangement member 330 arranging the first light guides 310 and the second light guides 320 that guide the light from the light source 60 to the optical sensor 10. The arrangement member 330 is an assembly including the first light guides 310 arranged in the mold 2000 so as to be capable of receiving the light from the light source 60 and the second light guides 320 arranged in the mold 2000 so as to be capable of irradiating the optical sensor 10. The arrangement member 330 constitutes an arrangement network for guiding the light from the light source 60 to the optical sensor 10. The arrangement member 330 is disposed such that the light-emitting portions 313 of the first light guides 310 and the light-receiving portions 321 of the second light guides 320 project out of the mold 2000. After Step S12 ends, the manufacturing method proceeds to a process at Step S13.

As illustrated in Process ST13 in FIG. 13, Step S13 of the manufacturing method is a process of forming the housing 200 by filling the periphery of the arrangement member 330 with a filling member 250. At Step S13, the periphery of the arrangement member 330 in the mold 2000 is filled with the filling member 250 to form the ring-shaped housing 200 that accommodates therein the arrangement member 330. The filling member 250 is a material for forming the housing 200, and contains a filling material such as powder or a liquid. Step S13 is a process of integrating the first light guides 310 and the second light guides 320 in the state of being embedded in the housing 200, using, for example, an insert molding technique. Thus, at Step S13, the material filling the periphery of the arrangement member 330 can be solidified to form the housing 200 where the ends of the first light guides 310 and the second light guides 320 project in a brush-like manner from the inner peripheral surface 210.

As described above, the method for manufacturing the detection device 1 enables the manufacturing of the detection device 1 in which the light-emitting portions 313 of the first light guides 310 projecting from the housing 200 irradiate the finger Fg, and the light received by the light-receiving portions 321 of the second light guides 320 projecting from the housing 200 is emitted to the optical sensor 10. Thus, the manufacturing method enables the manufacturing of the detection device 1 that can measure the light emitted from a plurality of locations of the housing 200 using one optical sensor 10, and therefore, can contribute to the improvement of the measurement accuracy of the biometric information. The manufacturing method can improve the irradiation area of the light source 60 in the housing 200 by producing the detection device 1 that can guide the light from the light source 60 using the first light guides 310 and emit the light from different positions. As a result, the manufacturing method enables the manufacturing of the detection device 1 that can measure the biometric information from the range where the first light guides 310 are in contact with the measurement target, and therefore, can improve the measurement accuracy of the biometric information when the detection device 1 is worn on the measurement target.

In the processing procedure illustrated in FIG. 12, the case has been described where the processes at Step S12 and Step S13 are performed after the light source 60 and an optical sensor 100 are arranged at Step S11, but the processing procedure is not limited to this case. For example, the processing procedure illustrated in FIG. 12 may be a procedure to perform the process of arranging the light source 60 and the optical sensor 100 in the housing 200 after performing the processes at Step S12 and Step S13 to embed the light source 60 and the optical sensor 100 in the housing 200.

In the processing procedure illustrated in FIG. 12, the ring-shaped housing 200 is formed so as to embed therein the arrangement member 330 at Step S13, but Step S13 is not limited thereto. For example, at Step S13, the housing 200 having, for example, a band shape or a string shape may be formed of a deformable filling member so as to be wrappable around a human body HB, such as the finger Fg, a wrist, or an arm.

Modification of First Embodiment

The detection device 1 according to the first embodiment has been described for the case where the light source 60 and the optical sensor 10 are arranged in the opposed positions in the housing 200. However, the arrangement is not limited to this case. In the detection device 1, the light source 60 and the optical sensor 10 may be arranged in positions not opposed to each other in the housing 200, or may be arranged side by side in the housing 200. In this case, in the housing 200 of the detection device 1, the light-receiving portion 311 of each of the first light guides 310A, 310B, 310C, and 310D only needs to be opposed to the light source 60, and the light-emitting portion 323 of each of the second light guides 320A, 320B, 320C, 320D only needs to be opposed to the photodiodes PD of the optical sensor 10.

The detection device 1 according to first embodiment has been described for the case where the optical fibers are used as the first and the second light guides 310 and 320 as illustrated in FIG. 11, but the first and the second light guides 310 and 320 are not limited to this case. The detection device 1 can use light-guiding cables or the like as the first and the second light guides 310 and 320.

Figure 14:
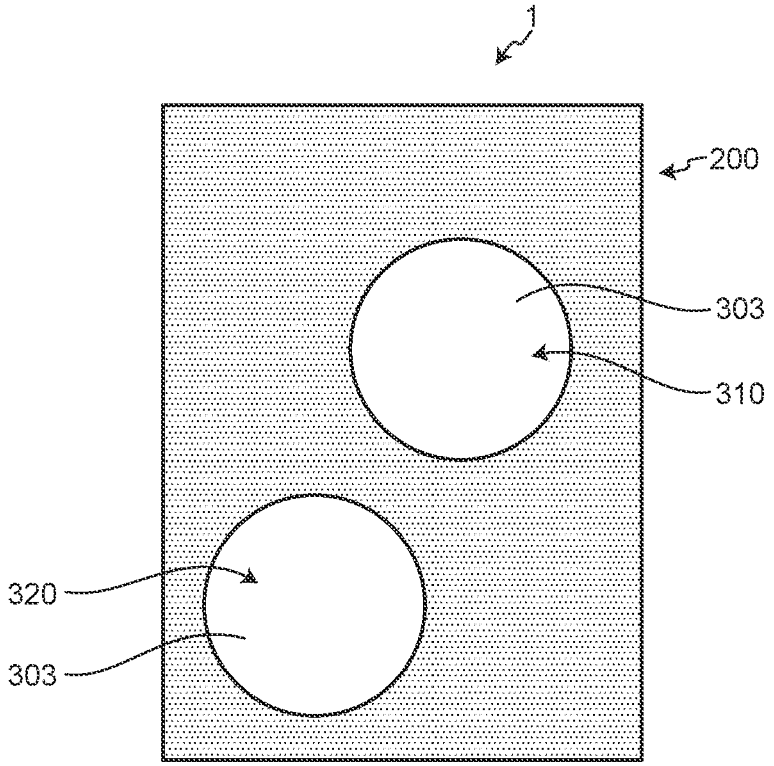
FIG. 14 is a schematic sectional view obtained by enlarging a portion of the housing of the detection device according to a modification of the first embodiment.

FIG. 14 is a schematic sectional view obtained by enlarging a portion of the housing 200 of the detection device according to a modification of the first embodiment. As illustrated in FIG. 14, the detection device 1 may use light-guiding cables 303 as the first and the second light guides 310 and 320. The housing 200 is formed of a material having a higher refractive index than those of the first and the second light guides 310 and 320. In this case, by making the refractive index of the housing 200 higher than that of the cables 303, the detection device 1 can prevent the cables 303 from interfering with each other. That is, in the detection device 1, the cables 303 may serve as cores of an optical fiber, and the housing 200 around the cables 303 may serve as cladding of the optical fiber. This configuration allows the detection device 1 to simplify the first light guides 310 and the second light guides 320 accommodated in the housing 200.

Second Embodiment

Detection Device

Figure 15:
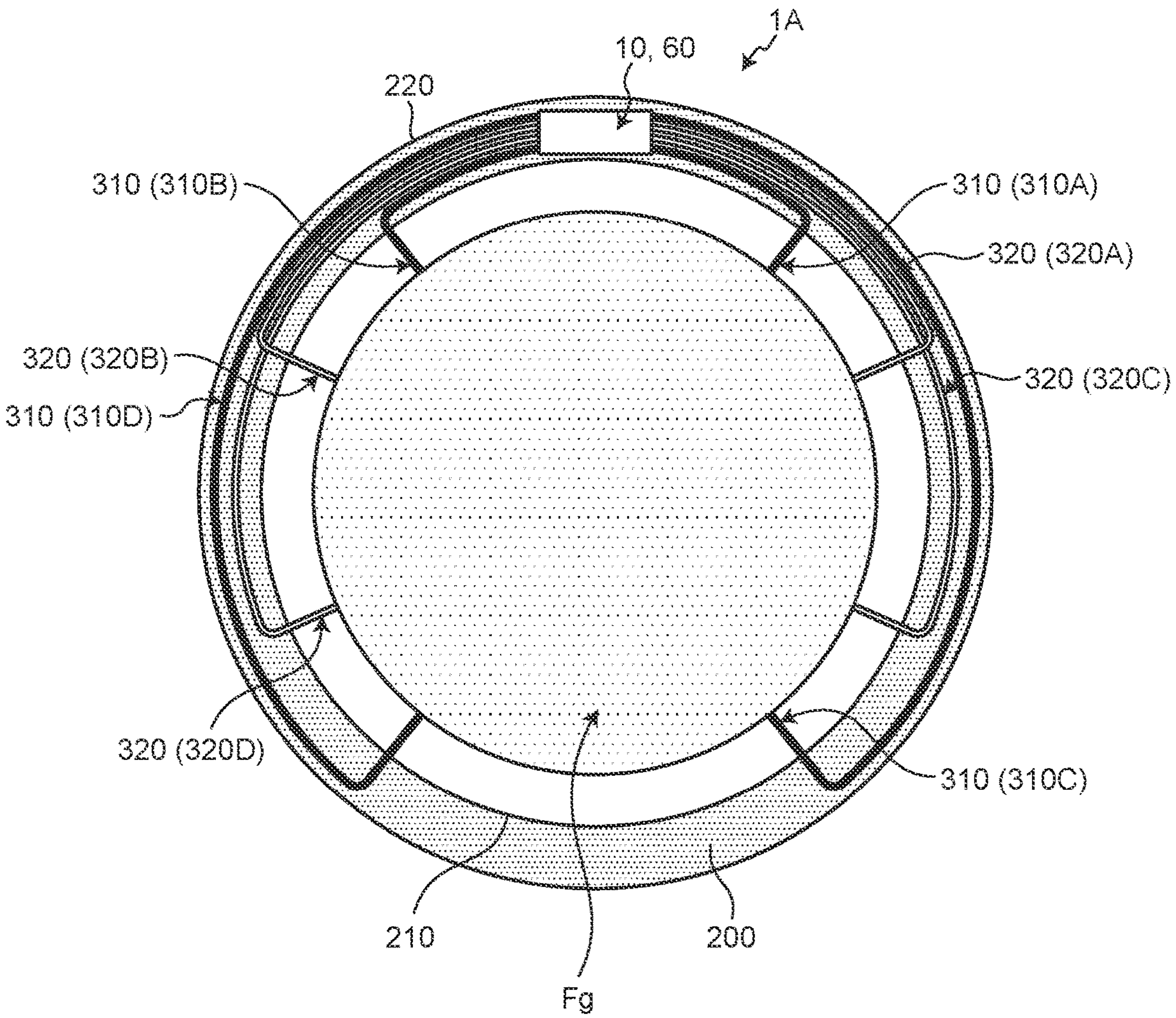
FIG. 15 is a schematic sectional view of a detection device according to a second embodiment.
Figure 16:
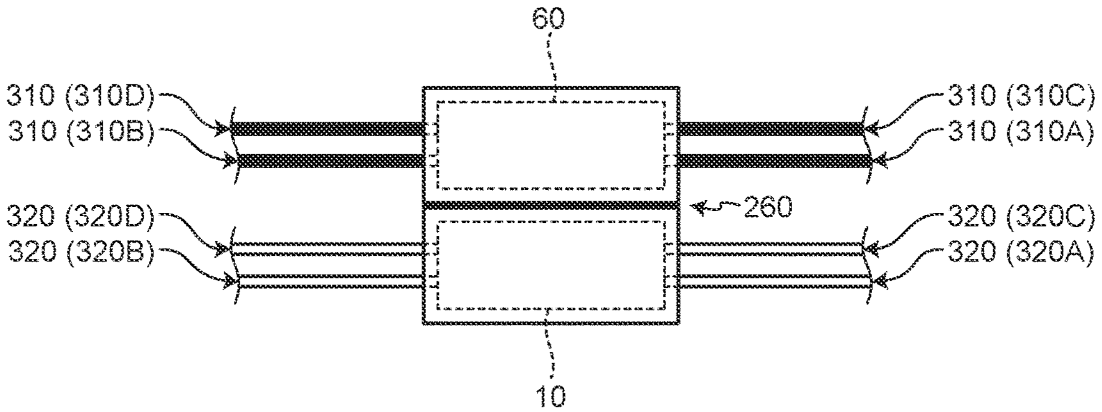
FIG. 16 is a diagram for explaining an arrangement example of a light source and the optical sensor according to the second embodiment.

FIG. 15 is a schematic sectional view of a detection device 1A according to a second embodiment. FIG. 16 is a diagram for explaining an arrangement example of the light source 60 and the optical sensor 10 according to the second embodiment.

As illustrated in FIG. 15, the detection device 1A includes the housing 200, the light source 60, the optical sensor 10, the first light guides 310, and the second light guides 320. In one example illustrated in FIG. 15, the four first light guides 310A, 310B, 310C, and 310D and the four second light guides 320A, 320B, 320C, and 320D of the first embodiment described above are illustrated in the detection device 1A.

The light source 60 and the optical sensor 10 are provided in parallel with each other in the ring-shaped housing 200. In the example illustrated in FIG. 15, the light source 60 and the optical sensor 10 are provided so as to overlap each other in the housing 200 between the inner peripheral surface 210 and the outer peripheral surface 220 of the housing 200. In detail, the detection device 1A arranges the light source 60 closer to the outer peripheral surface 220 (surface) of the housing 200 and the optical sensor 10 closer to the inner peripheral surface 210 (inner face) of the housing 200. In the present embodiment, the case of the detection device 1A is described where the light source 60 and the optical sensor 10 are provided so as to overlap each other in the housing 200 between the inner peripheral surface 210 and the outer peripheral surface 220 of the housing 200. However, the detection device 1A is not limited to this case. For example, the detection device 1A may arrange the light source 60 and the optical sensor 10 so as to be arranged in the circumferential direction between the inner peripheral surface 210 and the outer peripheral surface 220 of the housing 200.

As illustrated in FIG. 16, the light source 60 and the optical sensor 10 are integrated and provided in the housing 200. This configuration simplifies the assembling of the detection device 1A because the light source 60 and the optical sensor 10 only need be arranged in one location of the housing 200. The detection device 1A also interposes a light-blocking member 260 between the light source 60 and optical sensor 10 so as to prevent the optical sensor 10 from directly detecting the light emitted by the light source 60. The light-receiving side of the first light guide 310 faces the light source 60 so as to be capable of receiving the light emitted by the light source 60, and the light-emitting side of the first light guide 310 projects from inside the housing 200. The second light guides 320 are provided so that the light-emitting side thereof faces the photodiodes PD of the optical sensor 10.

The above has described the configuration example of the detection device 1A according to the present embodiment. The configuration described above using FIGS. 15 and 16 is merely an example, and the configuration of the detection device 1A according to the present embodiment is not limited to the example. The configuration of the detection device 1A according to the present embodiment can be flexibly modified according to specifications and operations.

Detection Example of Detection Device According to Second Embodiment

The following describes a detection example of the detection device 1A worn on the finger Fg. In the same manner as in the first embodiment, in the detection device 1A, the ends of the first light guides 310 and the second light guides 320 project in a brush-like manner from the inner peripheral surface 210 of the housing 200, and the finger Fg is inserted toward inside the housing 200. With this configuration, when the detection device 1A is worn on the finger Fg, the ends of the first light guides 310 and the second light guides 320 make point contact with the finger Fg.

The detection device 1A turns on the light source 60 at the time of detection while being worn on the finger Fg. In the detection device 1A, the light-receiving portion 311 of each of the first light guides 310A, 310B, 310C, and 310D receives the light emitted by the light source 60 that is turned on. The detection device 1A emits the light guided through the light-guiding portion 312 by each of the first light guides 310A, 310B, 310C, and 310D from the light-emitting portion 313 toward the finger Fg. Through this operation, the detection device 1A can emit the light emitted by one light source 60 from the first light guides 310A, 310B, 310C, and 310D in different areas (projection positions) on the inner peripheral surface 210 of the housing 200.

The detection device 1A receives, for example, the light reflected by the finger Fg at the light-receiving portions 321 of the second light guides 320A, 320B, 320C, and 320D, and guides the received light in the light-guiding portions 322 toward the optical sensor 10. The detection device 1A emits the light guided through the light-guiding portion 322 by each of the light-guiding portions 322 of the second light guides 320A, 320B, 320C, 320D from the light-emitting portion 323 toward the optical sensor 10. The detection device 1A detects the biometric information on the finger Fg based on the amount of light detected by each of the photodiodes PD of the optical sensor 10, and stores the detected biometric information in, for example, the storage circuit 46.

As described above, the detection device 1A can obtain the same operational advantages as those of the detection device 1. In addition, the light source 60 and the optical sensor 10 can be provided in parallel with each other in the ring-shaped housing 200 of the detection device 1A. As a result, in the detection device 1A, the first light guides 310 and the second light guides 320 are made easier to be assembled with the light source 60 and the optical sensor 10, thus being able to restrain the production efficiency from decreasing, even with a smaller size.

In the second embodiment described above, the light source 60 and the optical sensor 10 are provided in parallel with each other in the ring-shaped housing 200, but may be integrally formed into a modular structure. This structure can reduce the production cost of the detection device 1 because the light source 60 and the optical sensor 10 can be integrally molded.

Third Embodiment

Detection Device

Figure 17:
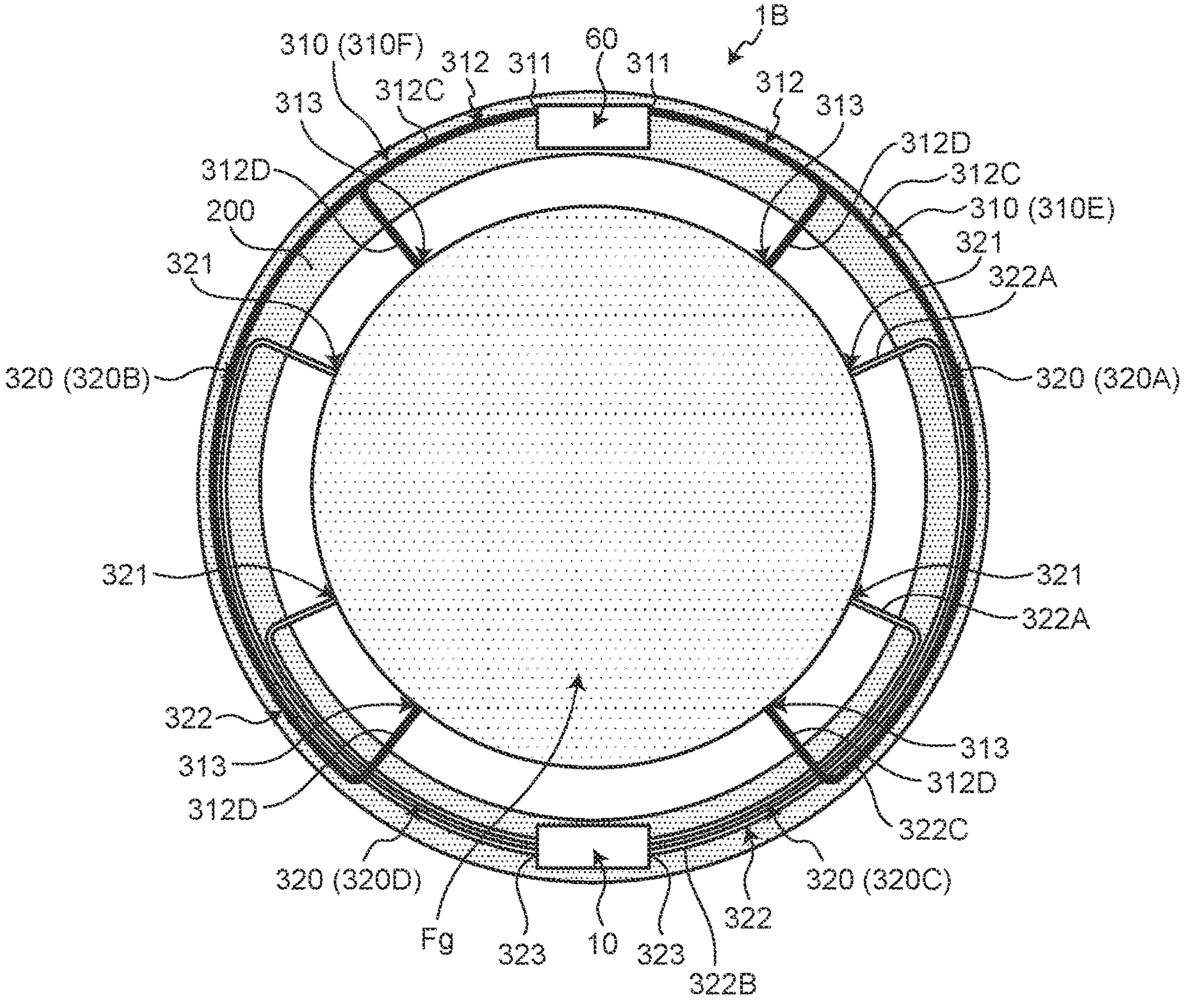
FIG. 17 is a schematic sectional view of a detection device according to a third embodiment.

FIG. 17 is a schematic sectional view of a detection device 1B according to a third embodiment. As illustrated in FIG. 17, a detection device 1BA includes the ring-shaped housing 200, the light source 60, the optical sensor 10, the first light guides 310, and the second light guides 320. In one example illustrated in FIG. 17, the detection device 1B has the same basic configuration as that of the first embodiment described above, but differs from the first embodiment in the configuration of the first light guides 310 and the second light guides 320.

The detection device 1B includes the line-shaped first light guides 310. The light-receiving side of each of the first light guides 310 faces the light source 60 so as to be capable of receiving the light emitted by the light source 60, and the light-emitting side of the first light guide 310 projects from inside the housing 200. The example illustrated in FIG. 17 illustrates a case where the detection device 1B includes two first light guides 310E and 310F. Hereinafter, when the first light guides 310E and 310F are not distinguished from each other, they are each referred to as "first light guide 310".

The first light guide 310 includes the light-receiving portion 311, the light-guiding portion 312, and the light-emitting portions 313. The light-receiving portion 311 is an end on the light-receiving side of the first light guide 310 provided in the housing 200, and receives the light emitted by the light source 60. The light-guiding portion 312 includes a body 312C embedded in the housing 200 and a plurality of branches 312D branched from the body 312C. The body 312C guides the light received from the light source 60 to each of the branches 312D. Each of the branches 312D projects from inside to outside the housing 200, and an end of the branch 312D serves as the light-emitting portion 313. The branch 312D includes a portion that is bent from an end of the body 312C toward inside the housing 200 so as to draw a curve and projects from the housing 200. The light-guiding portion 312 is bent between the body 312C and the branches 312D so as not to hinder the guiding of the light. The light-emitting portion 313 is an end on the light-emitting side of the first light guide 310 that irradiates the finger Fg or the like located inside the housing 200 with the light guided by the light-guiding portion 312. The light-emitting portion 313 is a portion where the first light guide 310 makes point contact with the finger Fg when the housing 200 is worn on the finger Fg, and emits the guided light toward the finger Fg.

The detection device 1B includes the line-shaped second light guides 320. Each of the second light guides 320 is formed in a line shape capable of receiving the light emitted by the light-emitting portion 313 of the first light guide 310 and guiding the received light.

The second light guide 320 includes the light-receiving portion 321, the light-guiding portion 322, and the light-emitting portion 323. The light-receiving portion 311 is an end on the light-receiving side of the second light guide 320 that projects out of the housing 200 and receives the light emitted by the light-emitting portion 313 of the first light guide 310. The light-receiving portion 321 is a portion where the second light guide 320 makes point contact with the finger Fg when the housing 200 is worn on the finger Fg, and receives, for example, the light reflected by the finger Fg and the direct light emitted by the nearby light-emitting portion 313 of each of the first light guides 310E and 310F. The light-guiding portion 322 includes the projection 322A projecting from inside to outside the housing 200 and the body 322B embedded in the housing 200. Each of the projections 322A projects from inside to outside the housing 200, and an end of the projection 322A serves as the light-receiving portion 321. Each of the light-guiding portions 322 is bent between the projection 322A and the body 322B so as not to hinder the guiding of the light. The light-emitting portion 323 is an end on the light-emitting side of the second light guide 320 that irradiates the optical sensor 10 with the light guided by the light-guiding portion 312. In the same manner as in the first embodiment, the light-emitting portion 323 irradiates predetermined one of the photodiodes PD of the optical sensor 10 with the light guided in the second light guide 320. That is, the light-emitting portion 323 can irradiate the optical sensor 10 with the light received in an area on the inner peripheral surface 210 of the housing 200 where the light-receiving portion 321 projects.

The above has described the configuration example of the detection device 1B according to the present embodiment. The configuration described above using FIG. 17 is merely an example, and the configuration of the detection device 1B according to the present embodiment is not limited to the example. The configuration of the detection device 1B according to the present embodiment can be flexibly modified according to specifications and operations.

In the example illustrated in FIG. 17, the case has been described where the detection device 1B includes the second light guides 320A, 320B, 320C, 320D described above. However, the detection device 1B is not limited to this case. For example, the detection device 1B may branch the second light guide 320 in the same manner as the first light guide 310. In this case, for example, a sensor that can acquire detailed waveforms of, for example, time/optical transmittance relations only needs to be used as the optical sensor 10.

Detection Example of Detection Device According to Third Embodiment

The following describes a detection example of the detection device 1B worn on the finger Fg. In the same manner as in the first embodiment, in the detection device 1B, the ends of the first light guides 310 and the second light guides 320 project in a brush-like manner from the inner peripheral surface 210 of the housing 200, and the finger Fg is inserted toward inside the housing 200. With this configuration, when the detection device 1B is worn on the finger Fg, the ends of the first light guides 310 and the second light guides 320 make point contact with the finger Fg.

The detection device 1B turns on the light source 60 at the time of detection while being worn on the finger Fg. In the detection device 1B, the light-receiving portion 311 of each of the first light guides 310E and 310F receives the light emitted by the light source 60 that is turned on. The detection device 1B emits the light guided through the light-guiding portion 312 by each of the first light guides 310E and 310F toward the finger Fg from the light-emitting portions 313 serving as the distal ends of the branches 312D. Through this operation, the detection device 1B can emit the light emitted by one light source 60 from the first light guides 310E and 310F in different areas (projection positions) on the inner peripheral surface 210 of the housing 200.

The detection device 1B receives, for example, the light reflected by the finger Fg at the light-receiving portion 321 at the distal end of a projection 322D of each of two second light guides 320E and two second light guides 320F having different lengths, and guides the received light in the light-guiding portion 322 toward the optical sensor 10. The detection device 1B emits the light guided by each of the light-guiding portions 322 of the two second light guides 320E and the two second light guides 320F through the light-guiding portion 322 from the light-emitting portion 323 toward the optical sensor 10. The detection device 1B detects the biometric information on the finger Fg based on the amount of light detected by each of the photodiodes PD of the optical sensor 10, and stores the detected biometric information in, for example, the storage circuit 46.

As described above, the detection device 1B can obtain the same operational advantages as those of the detection device 1. In the detection device 1B, the first light guide 310 includes the body 312C and the branches 312D branched from the body 312C, and the distal ends of the branches 312D project from the different areas on the inner peripheral surface 210 (one surface) of the housing 200. Since this configuration allows the detection device 1B to emit the light from the light-emitting portions 313 serving as the distal ends of the branches 312D that are more in number than the first light guides 310, the number of first light guides 300 can be made smaller than that of the light-emitting portions 313, thus being able to contribute to reduction in size and cost of the housing 200.

Fourth Embodiment

Detection Device

Figure 18:
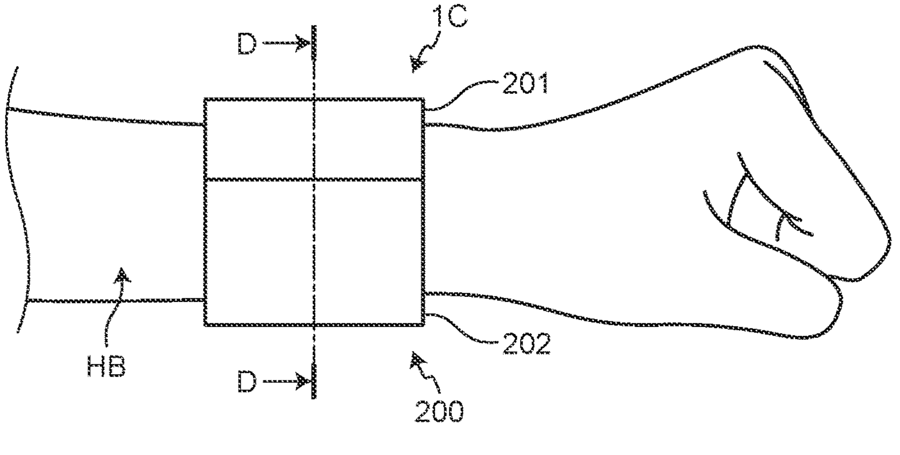
FIG. 18 is a schematic view illustrating an example of an external view of a state where a human body is accommodated in a detection device according to a fourth embodiment, as viewed from the lateral side of the housing.
Figure 19:
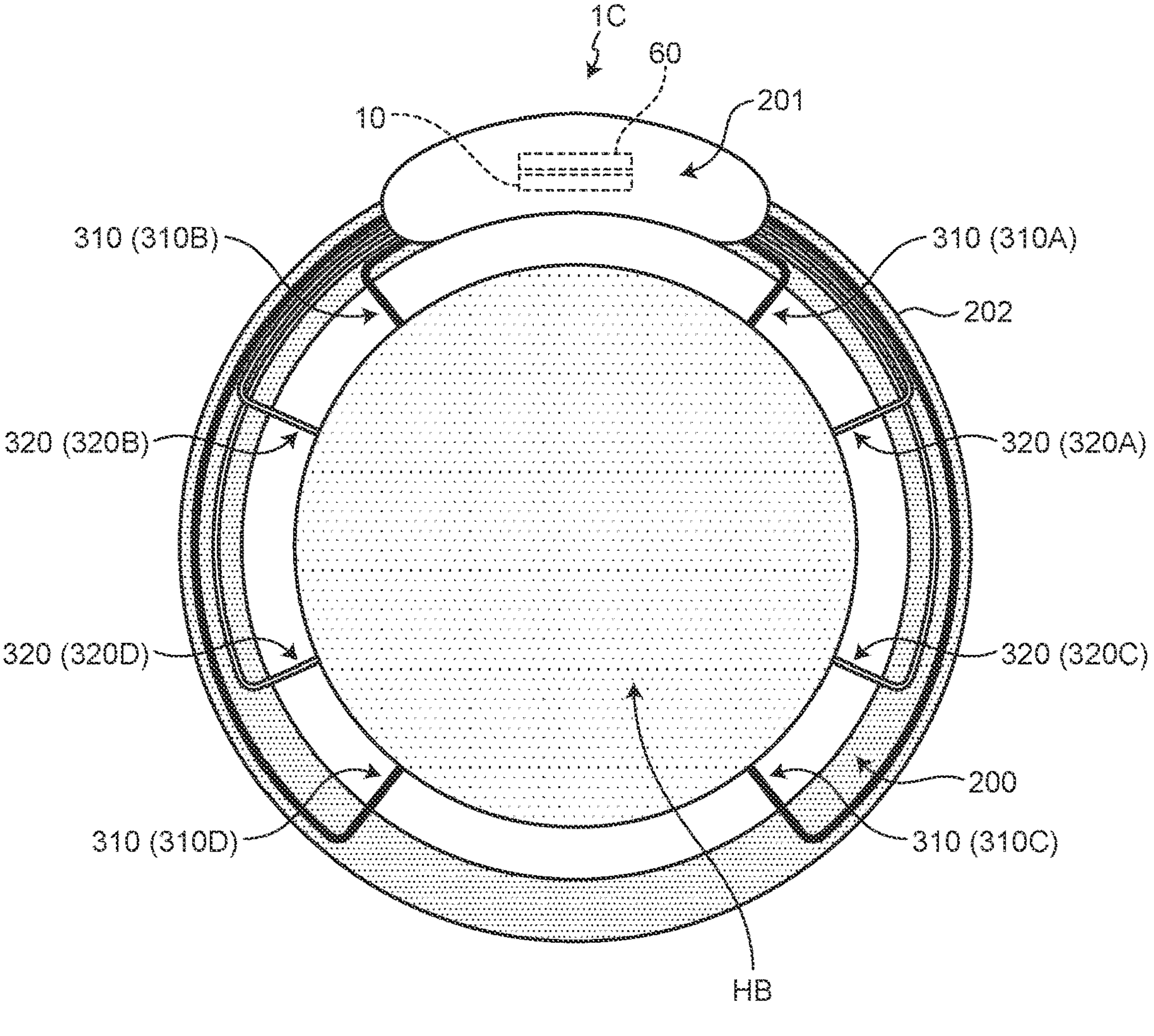
FIG. 19 is a schematic sectional view along section D-D illustrated in FIG. 18.

FIG. 18 is a schematic view illustrating an example of an external view of a state where the human body is accommodated in a detection device according to a fourth embodiment, as viewed from the lateral side of the housing. FIG. 19 is a schematic sectional view along section D-D illustrated in FIG. 18.

A detection device 1C illustrated in FIGS. 18 and 19 is a ring-shaped device that can be worn on and removed from the human body HB, and is worn on the arm of the human body HB. The human body HB is the body of the person to be authenticated whose identity is checked by the detection device 1, and includes wrists, arms, legs, and the like. In the present embodiment, a case will be described where the detection device 1C is a smartwatch, but the detection device 1C may be a wristwatch, a wristband, or the like. The detection device 1C can detect the biometric information on the living body from the human body HB wearing the detection device 1C.

As illustrated in FIG. 19, the detection device 1C includes the housing 200, the light source 60, the optical sensor 10, the first light guides 310, and the second light guides 320. The detection device 1C includes the four first light guides 310A, 310B, 310C, and 310D and the four second light guides 320A, 320B, 320C, and 320D of the present embodiment described above. The detection device 1C is a device that includes a battery (not illustrated) in the housing 200, and is operated by power of the battery.

The housing 200 includes a body 201 and a wearable portion 202. The body 201 has a structure of, for example, a display mechanism or a pointer mechanism (which are not illustrated) for displaying the time, the date, or the like to the person to be authenticated. The body 201 accommodates therein the light source 60 and the optical sensor 10. The wearable portion 202 is a belt for wearing the body 201 on the living body HB, and is provided on the body 201. The wearable portion 202 is provided therein with the first light guides 310 and the second light guides 320. The light-emitting portions 313 of the first light guides 310 and the light-receiving portions 321 of the second light guides 320 project from a contact surface side of the wearable portion 202 with the human body HB. With this configuration, when the housing 200 of the detection device 1C is worn on the human body HB, the light-emitting portions 313 of the first light guides 310 and the light-receiving portions 321 of the second light guides 320 make point contact with the human body HB.

The light source 60 and the optical sensor 10 are provided in parallel with each other in the body 201 of the housing 200. The light source 60 is provided in the body 201, and is opposed to the light-receiving portions 311 of the first light guides 310 in the body 201. For example, a backlight for a clock, a display device, and the like provided in the body 201 may be used as the light source 60. The optical sensor 10 is provided in the body 201, and is opposed to the light-emitting portions 323 of the second light guides 320 in the body 201.

The above has described the configuration example of the detection device 1C according to the present embodiment. The configuration described above using FIGS. 18 and 19 is merely an example, and the configuration of the detection device 1C according to the present embodiment is not limited to the example. The configuration of the detection device 1C according to the present embodiment can be flexibly modified according to specifications and operations.

Detection Example of Detection Device According to Fourth Embodiment

The following describes a detection example of the detection device 1C worn on the human body HB. In the detection device 1C, the ends of the first light guides 310 and the second light guides 320 project in a brush-like manner from inside the wearable portion 202 of the housing 200. When the detection device 1C is worn on the human body HB, the ends of the first light guides 310 and the second light guides 320 make point contact with the human body HB.

The detection device 1C turns on the light source 60 at the time of detection while being worn on the human body HB. In the detection device 1C, the light-receiving portion 311 of each of the first light guides 310A, 310B, 310C, and 310D receives the light emitted by the light source 60 that is turned on. The detection device 1C emits the light guided through the light-guiding portion 312 by each of the first light guides 310A, 310B, 310C, and 310D from the light-emitting portion 313 toward the human body HB. Through this operation, the detection device 1C can emit the light emitted by one light source 60 from the first light guides 310A, 310B, 310C, and 310D in different areas (projection positions) of the wearable portion 202 of the housing 200.

The detection device 1C receives, for example, light reflected by the human body HB at the light-receiving portions 321 of the second light guides 320A, 320B, 320C, and 320D, and guides the received light in the light-guiding portions 322 toward the optical sensor 10. The detection device 1C emits the light guided through the light-guiding portion 322 by each of the light-guiding portions 322 of the second light guides 320A, 320B, 320C, 320D from the light-emitting portion 323 toward the optical sensor 10. The detection device 1C detects the biometric information on the human body HB based on the amount of light detected by each of the photodiodes PD of the optical sensor 10, and stores the detected biometric information in, for example, the storage circuit 46.

As described above, when the detection device 1C is worn on the human body HB, the light-emitting portions 313 of the first light guides 310 projecting from the housing 200 and in point contact with the human body HB irradiate the human body HB, and the light received by the light-receiving portions 321 of the second light guides 320 projecting from the housing 200 is emitted to the optical sensor 10. This operation allows the detection device 1C to measure the light emitted from a plurality of locations of the housing 200 using one optical sensor 10. Therefore, the detection device 1C can improve the measurement accuracy of the biometric information. The detection device 1C can improve the irradiation area of the light source 60 in the housing 200 by guiding the light from the light source 60 using the first light guides 310 and emitting the light from different positions. As a result, the detection device 1C can measure the biometric information from a range where the first light guides 310 are in contact with the measurement target. Therefore, the measurement accuracy of the biometric information when the detection device 1C is worn on the measurement target can be improved. In addition, the detection device 1C can reduce the physical restraint on the body and improve the wearability by causing the ends of the first light guides 310 and the second light guides 320 to make point contact with the human body HB.

Fifth Embodiment

Detection Device

Figure 20:
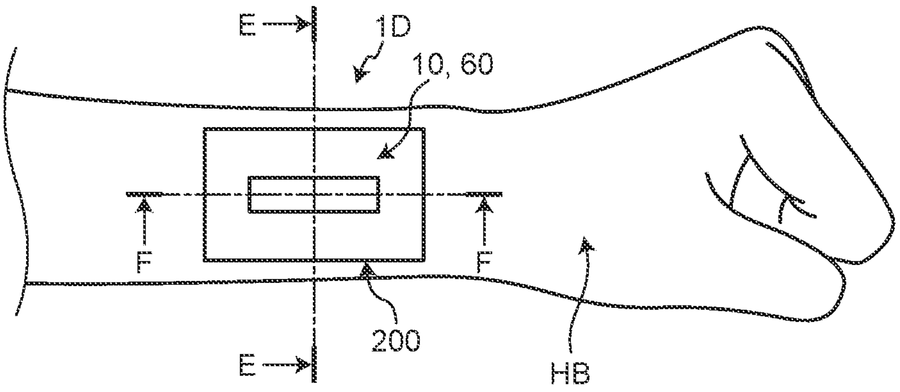
FIG. 20 is a schematic view illustrating an example of an external view of a state where the human body is wearing a detection device according to a fifth embodiment, as viewed from the lateral side of the housing.
Figure 21:
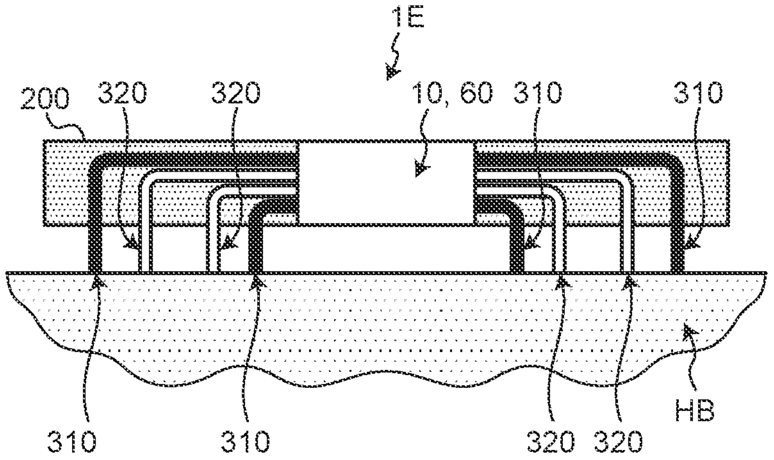
FIG. 21 is a schematic sectional view along section E-E illustrated in FIG. 20.
Figure 22:
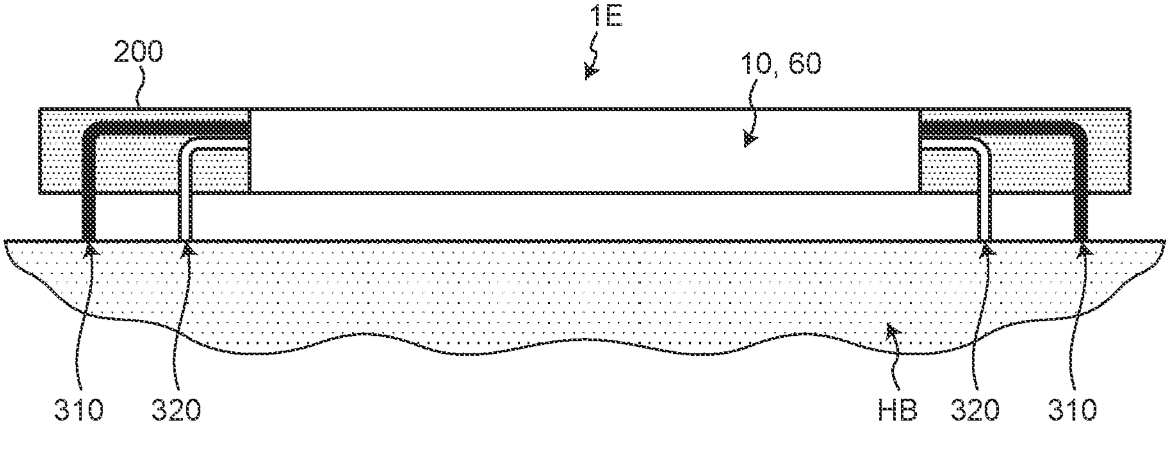
FIG. 22 is a schematic sectional view along section F-F illustrated in FIG. 20.

FIG. 20 is a schematic view illustrating an example of an external view of a state where the human body is wearing a detection device according to a fifth embodiment, as viewed from the lateral side of the housing. FIG. 21 is a schematic sectional view along section E-E illustrated in FIG. 20. FIG. 22 is a schematic sectional view along section F-F illustrated in FIG. 20.

A detection device 1D illustrated in FIGS. 20 to 22 is a card-shaped device that can be worn on and removed from the human body HB. The detection device 1D has a configuration capable of being worn on and removed from a surface of the human body HB by being worn on the surface of the human body HB using a wearing member, a belt, and the like, or placed on the surface of the human body HB. The detection device 1D can detect the biometric information on the living body from the human body HB wearing the detection device 1D.

As illustrated in FIGS. 21 and 22, the detection device 1D includes the housing 200, the light source 60, the optical sensor 10, the first light guides 310, and the second light guides 320. The detection device 1D includes the four first light guides 310 and the four second light guides 320 of the present embodiment described above. The detection device 1D is a device that includes a battery (not illustrated) in the housing 200, and is operated by power of the battery.

The housing 200 is formed of a synthetic resin into the card shape. The housing 200 accommodates therein the light source 60, the optical sensor 10, the first light guides 310, and the second light guides 320. The housing 200 is provided therein with the first light guides 310 and the second light guides 320. The light-emitting portions 313 of the first light guides 310 and the light-receiving portions 321 of the second light guides 320 project from a contact surface side of the housing 200 with the human body HB. With this configuration, when the housing 200 of the detection device 1D is worn on the human body HB, the light-emitting portions 313 of the first light guides 310 and the light-receiving portions 321 of the second light guides 320 make point contact with the human body HB.

The light source 60 and the optical sensor 10 are provided in parallel with each other in the body 201 of the housing 200, as described above in the present embodiment. The light source 60 is provided in the body 201, and is opposed to the light-receiving portions 311 of the first light guides 310 in the body 201. The optical sensor 10 is provided in the body 201, and is opposed to the light-emitting portions 323 of the second light guides 320 in the body 201.

The above has described the configuration example of the detection device 1D according to the present embodiment. The configuration described above using FIGS. 20 to 22 is merely an example, and the configuration of the detection device 1D according to the present embodiment is not limited to the example. The configuration of the detection device 1D according to the present embodiment can be flexibly modified according to specifications and operations.

Detection Example of Detection Device According to Fifth Embodiment

The following describes a detection example of the detection device 1D worn on the human body HB. In the detection device 1D, the ends of the first light guides 310 and the second light guides 320 project in a brush-like manner from the contact surface side of the housing 200 with the human body HB. When the detection device 1D is worn on the human body HB, the ends of the first light guides 310 and the second light guides 320 make point contact with the human body HB.

The detection device 1D turns on the light source 60 at the time of detection while being worn on the human body HB. In the detection device 1D, the light-receiving portion 311 of each of the first light guides 310 receives the light emitted by the light source 60 that is turned on. The detection device 1D emits the light guided through the light-guiding portion 312 by each of the first light guides 310 from the light-emitting portion 313 toward the human body HB. Through this operation, the detection device 1D can emit the light emitted by one light source 60 from the first light guides 310 in different areas (projection positions) on the contact surface of the housing 200.

The detection device 1D receives, for example, the light reflected by the human body HB at the light-receiving portions 321 of the second light guides 320, and guides the received light in the light-guiding portions 322 toward the optical sensor 10. The detection device 1D emits the light guided through the light-guiding portion 322 by each of the light-guiding portions 322 of the second light guides 320A, 320B, 320C, 320D from the light-emitting portion 323 toward the optical sensor 10. The detection device 1D detects the biometric information on the human body HB based on the amount of light detected by each of the photodiodes PD of the optical sensor 10, and stores the detected biometric information in, for example, the storage circuit 46.

As described above, when the detection device 1D is worn on the human body HB, the light-emitting portions 313 of the first light guides 310 projecting from the housing 200 and in point contact with the human body HB irradiate the human body HB, and the light received by the light-receiving portions 321 of the second light guides 320 projecting from the housing 200 is emitted to the optical sensor 10. This operation allows the detection device 1D to measure the light emitted from a plurality of locations of the housing 200 using one optical sensor 10. Therefore, the detection device 1D can improve the measurement accuracy of the biometric information. The detection device 1D can improve the irradiation area of the light source 60 in the housing 200 by guiding the light from the light source 60 using the first light guides 310 and emitting the light from different positions. As a result, the detection device 1D can measure the biometric information from a range where the first light guides 310 are in contact with the measurement target. Therefore, the measurement accuracy of the biometric information when the detection device 1D is worn on the measurement target can be improved. In addition, the detection device 1D does not require the housing 200 to be always worn on the human body HB, and therefore, can improve the convenience.

The components in the embodiments described above can be combined with one another as appropriate. Other operational advantages accruing from the aspects described in the embodiments of the present disclosure that are obvious from the description herein, or that are conceivable as appropriate by those skilled in the art will naturally be understood as accruing from the present disclosure.

What is claimed is:

1. A detection device comprising:

a housing;

a light source provided in the housing;

an optical sensor provided in the housing;

a plurality of line-shaped first light guides provided in the housing and capable of guiding light emitted by the light source; and a plurality of line-shaped second light guides provided in the housing and capable of receiving the light guided by the first light guides and guiding the received light to the optical sensor, wherein a first light-receiving portion at one end of each of the first light guides faces the light source so as to be capable of receiving the light emitted by the light source, and a first light-emitting portion at another end of each of the first light guides projects from inside the housing, a second light-receiving portion at one end of each of the second light guides projects from inside the housing, and a second light-emitting portion at another end of each of the second light guides faces the optical sensor, the first light guide includes:

a first light-guiding portion extending inside the housing along a circumference direction of the housing; and a first projection that is a bent part of the first light guard and that projects toward a measurement target from inside the housing, and the second light guide includes:

a second light-guiding portion extending inside the housing along the circumference direction of the housing; and a second projection that is a bent part of the second light guard and that projects toward the measurement target from inside the housing.

2. The detection device according to claim 1, wherein each first light-emitting portion forms a respective first projection projecting from inside the housing, and is capable of making point contact with a measurement target wearing the housing, and each second light-receiving portion forms a respective second projection projecting from inside the housing, is capable of making point contact with the measurement target, and is configured to receive the light from the first light guide.

3. The detection device according to claim 1, wherein the housing is formed in a ring shape.

4. The detection device according to claim 3, wherein the light source and the optical sensor are provided in parallel with each other in the ring-shaped housing.

5. The detection device according to claim 1, wherein each of the first light guides comprises a respective first light-guiding portion and a plurality of first branches branched from one first light-guiding portion, and distal ends of the first branches project from different areas on one surface of the housing.

6. The detection device according to claim 1, wherein the first light guides and the second light guides are optical fibers.

7. The detection device according to claim 1, wherein the housing in contact with the first light guides and the second light guides is formed of a material having a higher refractive index than those of the first light guides and the second light guides.

* * * * *